(12) United States Patent
Wasielewski

(10) Patent No.: US 8,377,073 B2
(45) Date of Patent: Feb. 19, 2013

(54) METHOD OF DESIGNING ORTHOPEDIC IMPLANTS USING IN VIVO DATA

(76) Inventor: Ray Wasielewski, New Albany, OH (US)

( * ) Notice: Subject to any disclaimer, the term of this patent is extended or adjusted under 35 U.S.C. 154(b) by 838 days.

(21) Appl. No.: 12/348,285

(22) Filed: Jan. 3, 2009

(65) Prior Publication Data

US 2009/0264894 A1 Oct. 22, 2009

Related U.S. Application Data

(60) Provisional application No. 61/046,512, filed on Apr. 21, 2008, provisional application No. 61/199,545, filed on Nov. 18, 2008.

(51) Int. Cl.
*A61F 2/38* (2006.01)

(52) U.S. Cl. ............ 606/102; 623/20.15; 623/901; 623/908

(58) Field of Classification Search .......... 606/102; 600/424, 587, 595; 623/901, 909–923, 20.14–20.15; 703/11

See application file for complete search history.

(56) References Cited

U.S. PATENT DOCUMENTS

| | | | |
|---|---|---|---|
| 4,950,297 A | 8/1990 | Elloy et al. | |
| 5,470,354 A | 11/1995 | Hershberger et al. | |
| 5,533,519 A | 7/1996 | Radke et al. | |
| 6,205,411 B1 * | 3/2001 | DiGioia et al. | 703/11 |
| 6,932,842 B1 * | 8/2005 | Litschko et al. | 623/16.11 |
| 7,309,363 B2 | 12/2007 | Dietz | |
| 8,078,440 B2 * | 12/2011 | Otto et al. | 703/6 |
| 2002/0183656 A1 | 12/2002 | Levanoni et al. | |
| 2004/0064191 A1 * | 4/2004 | Wasielewski | 623/20.14 |
| 2004/0152972 A1 | 8/2004 | Hunter | |
| 2004/0162620 A1 | 8/2004 | Wyss | |
| 2005/0197814 A1 * | 9/2005 | Aram et al. | 703/11 |
| 2006/0036324 A1 | 2/2006 | Sachs et al. | |
| 2006/0136058 A1 | 6/2006 | Pietrzak | |
| 2007/0005145 A1 * | 1/2007 | Banks et al. | 623/23.42 |
| 2007/0066917 A1 | 3/2007 | Hodorek et al. | |
| 2007/0179626 A1 * | 8/2007 | de la Barrera et al. | 623/20.14 |
| 2009/0005708 A1 * | 1/2009 | Johanson et al. | 600/587 |

FOREIGN PATENT DOCUMENTS

| | | |
|---|---|---|
| WO | WO 2007/126918 A2 | 11/2007 |
| WO | PCT/US/09/06166 | 11/2009 |
| WO | WO 2010/059202 A1 | 5/2010 |
| WO | PCT/US2009/006166 | 6/2011 |

OTHER PUBLICATIONS

McConway et al, The use of a posterior lip augmentation device for a revision of recurrent dislocation after primary cemented Charnley/Charnley Elite total hip replacement, © 2007 British Editorial Society of Bone and Joint Surgery, J Bone Joint Surg (Br) 2007;89-B:1581-5, United Kingdom.

Flecher et al, Three-dimensional custom-designed cementless femoral stem for osteoarthritis secondary to congenital dislocation of the hip, © 2007 British Editorial Society of Bone and Joint Surgery, J Bone Joint Surg (Br) 2007;89-B:1586-91, United Kingdom.

(Continued)

*Primary Examiner* — Kevin T Truong
*Assistant Examiner* — Larry E Waggle, Jr.
(74) *Attorney, Agent, or Firm* — Taft Stettinius & Hollister LLP

(57) ABSTRACT

The present disclosure is directed to orthopedic implants and methods of designing orthopedic implants using in vivo data specific to an orthopedic implant or orthopedic trial. Specifically, the instant disclosure utilizes permanent orthopedic implants and orthopedic trials outfitted with pressure sensors to provide feedback regarding the position and magnitude of pressures exerted upon the devices to discern which design is preferable or which designs are preferable.

13 Claims, 22 Drawing Sheets

OTHER PUBLICATIONS

Glaser, et al., Clicking and Squeaking: in Vivo Sound and Separation Correlation of Different Bearing Surfaces, Center for Musculoskeletal Research, American Academy of Orthopaedic Surgeons, 2008, San Francisco, CA.

Glaser, et al., In vivo comparison of hip mechanics for minimally invasive versus traditional total hip arthroplasty, ScienceDirect, Clinical Biomechanics 23 (2008) 127-134, © Elsevier Ltd., USA.

Komistek, et al., In Vivo Comparison of Hip Separation After Metal-On-Metal or Metal-On-Polyethylene Total Hip Arthroplasty, © 2002, The Journal of Bone & Joint Surgery, vol. 84-A, No. 10, Oct. 2002, p. 1836-1841, USA.

Dennis, et al., "In vivo" determination of hip joint separation and the forces generated due to impact loading conditions, Journal of BioMechanics 34 (2001) 623-629, © 2001 Elsevier Science Ltd., USA.

Unknown, The Internation Society for Technology in Arthroplasty, 2009: Sponsor Prospectus, pp. 1-3, USA.

Pappas, et al., LCS—Mobility with Congruency, BioMechanics and Design Rationale: New Jersey LCS Knee Replacement System, prepared for 1993 DePuy Sales Training Seminars, USA.

\* cited by examiner

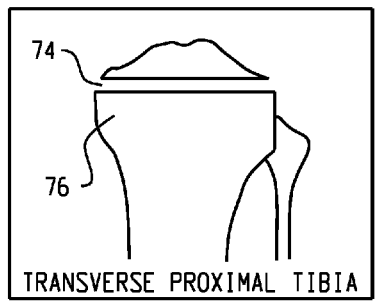 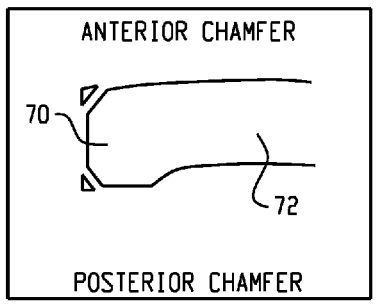 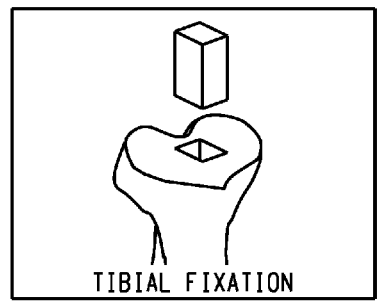
Fig. 7D     Fig. 7E     Fig. 7F
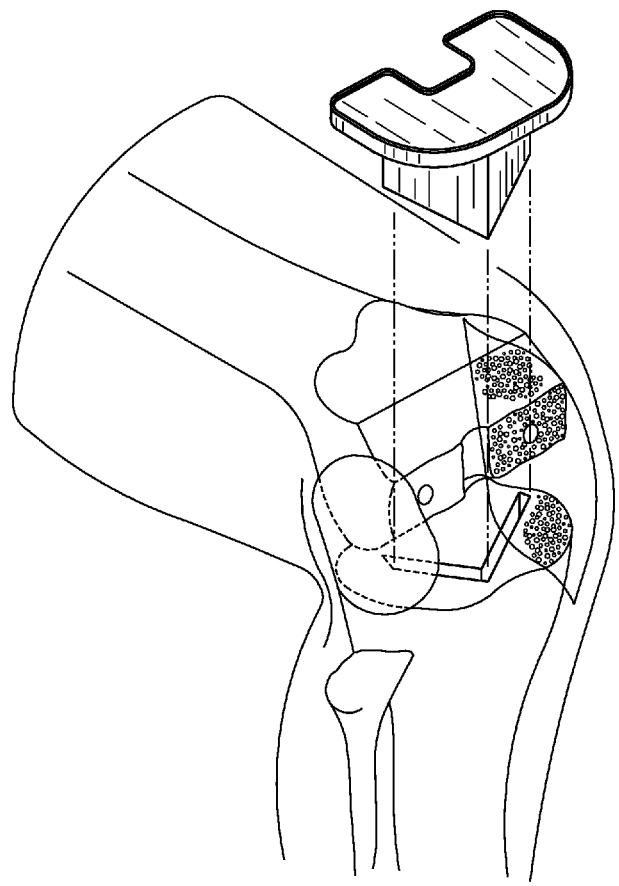
Fig. 8

METHOD OF DESIGNING ORTHOPEDIC IMPLANTS USING IN VIVO DATA

CROSS-REFERENCE TO RELATED APPLICATIONS

This application claims the benefit of U.S. Provisional Application Ser. No. 61/046,512, filed Apr. 21, 2008, and U.S. Provisional Application Ser. No. 61/199,545, filed Nov. 18, 2008, the disclosures of each of which are hereby incorporated by reference.

RELATED ART

1. Field of the Invention

The present invention is directed to orthopedic implants and methods of designing orthopedic implants using in vivo data specific to an orthopedic implant or orthopedic trial. Specifically, the instant invention may utilize permanent orthopedic implants and orthopedic trials (collectively, "implants") outfitted with pressure sensors to provide in vivo feedback regarding the position and magnitude of pressures exerted upon the devices to discern which design(s) is preferable.

2. Brief Discussion of Related Art

Orthopedic knee replacement systems are currently developed based on arthropometric studies of average bone shape, visual examination of used orthopedic implants, and simulated knee systems using computer aided design (CAD) software. In addition, orthopedic implants failures are examined by implant designers, which may result in design changes made to the proposed CAD orthopedic implant design(s). The resulting CAD designs are then manipulated by the CAD software to generate simulated data as to the kinematics of the artificial joint and possible wear data. But at no time are the proposed orthopedic implant designs tested in vivo to determine kinematics and the actual forces exerted upon the joint through its range of motion. Accordingly, prior art methods of designing orthopedic implants have suffered from the limitations associated with CAD software models to accurately predict periarticular forces, kinematics, and constraints.

Every arthritic natural knee undergoing total knee arthroplasty (TKA) has different muscle, tendon, and ligamentous abnormalities. In addition, different approaches for TKA release different ligamentous structures that also affect the periarticular knee forces and kinematics. But when modeling the knee using CAD software, the programmer must make considerable and likely erroneous boundary conditions to model periarticular structures. The instant invention addresses some of these shortcomings by gathering in vivo data directly from actual orthopedic implants using the same bone cuts that would be made during a knee replacement procedure. In this manner, the in vivo data objectively identifies to orthopedic designers which proposed implant design has the best kinematics and pressure distributions. Also, abnormally high forces on vulnerable implant features (e.g., a tibial insert post) can be determined prior to permanent implant failure. Accordingly, proposed orthopedic implant designs can be prioritized and further refined before adopting a preferred orthopedic implant design. In addition to using in vivo data to design and/or refine orthopedic implants, the instant invention also allows this in vivo data to be utilized to construct mathematical and CADCAM software models simulating and accurately reflecting natural movements of body parts. Accordingly, future modeling of orthopedic components may not utilize in vivo data directly, but rather rely on software modeled using actual in vivo data.

INTRODUCTION TO THE INVENTION

The present invention is directed to orthopedic implants and methods of designing orthopedic implants using in vivo data specific to the orthopedic implant or orthopedic trial. Specifically, the instant invention utilizes permanent orthopedics and orthopedic trials (collectively, "implants") outfitted with sensors (such as pressure sensors, accelerometers, vibration sensors, sound sensors, ultrasonic sensors, etc.) to provide feedback regarding the position of the implants, as well as the positions and magnitudes of pressures exerted upon the implants, when moved through an in vivo range of motion to discern which design(s) is preferable. In addition, permanent orthopedics and orthopedic trials (collectively, "implants") outfitted with sensors may provide feedback about contact area measurements throughout the range of movement of the prosthetic joint to, in exemplary form, ensure that contact areas are sufficient to decrease stresses and reduce wear between the contact surfaces of the joint. In other words, greater contact areas between joint components moving against one another generally translates into loads applied to the joint being less concentrated, thereby reducing wear associated with the contacting surfaces, such as polyethylene tibial tray inserts, for example.

BRIEF DESCRIPTION OF THE DRAWINGS

FIGS. 7A-7F are various views showing bone cuts to the tibia and femur during a knee arthroplasty procedure; and FIG. 8 is an elevated perspective view showing how a patient's tibia may be modified to receive a tibia tray;

DETAILED DESCRIPTION

The exemplary embodiments of the present invention are described and illustrated below to encompass methods of designing, selecting, and manufacturing orthopedic implants, as well as the resulting orthopedic implants themselves, in addition to methods to improve software simulations using actual in vivo data. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
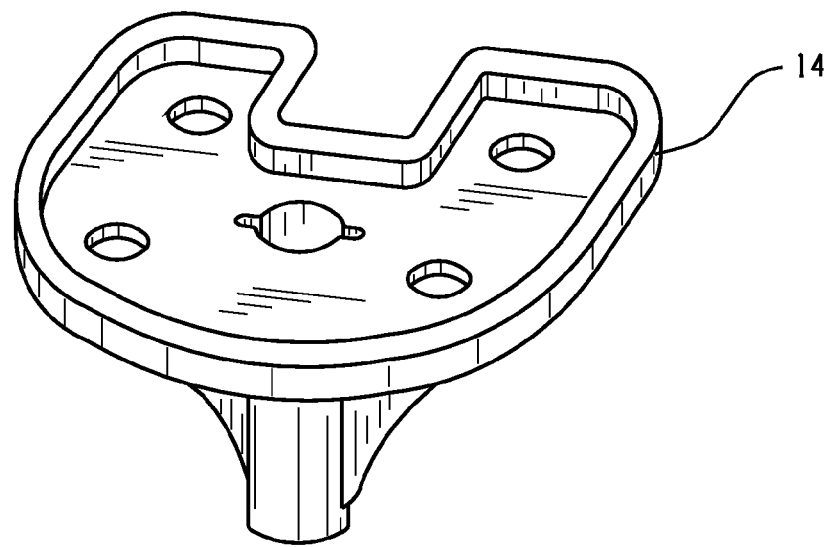
FIG. 1 is an elevated perspective view of an exemplary stereolithography tibial tray trial.
Figure 2:
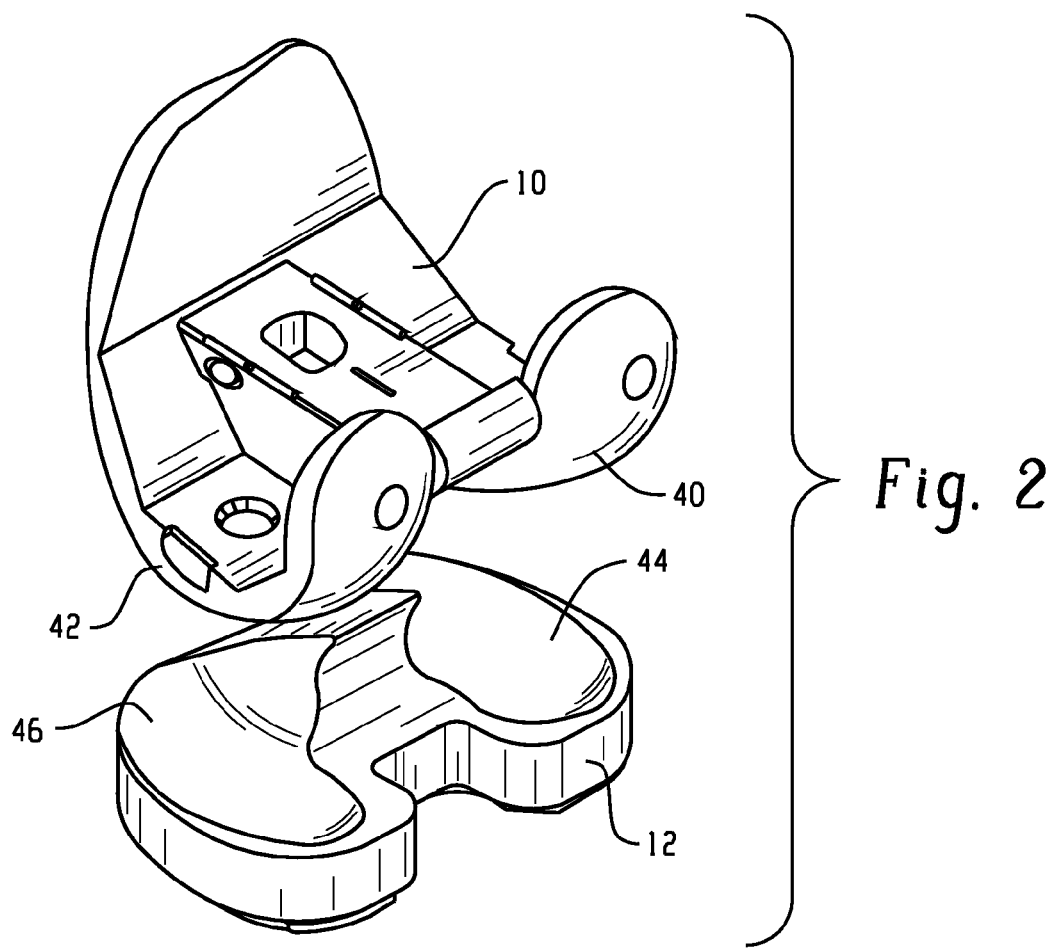
FIG. 2 is an exploded view of an exemplary stereolithography femoral trial and stereolithography tibial tray insert trial.
Figure 3:
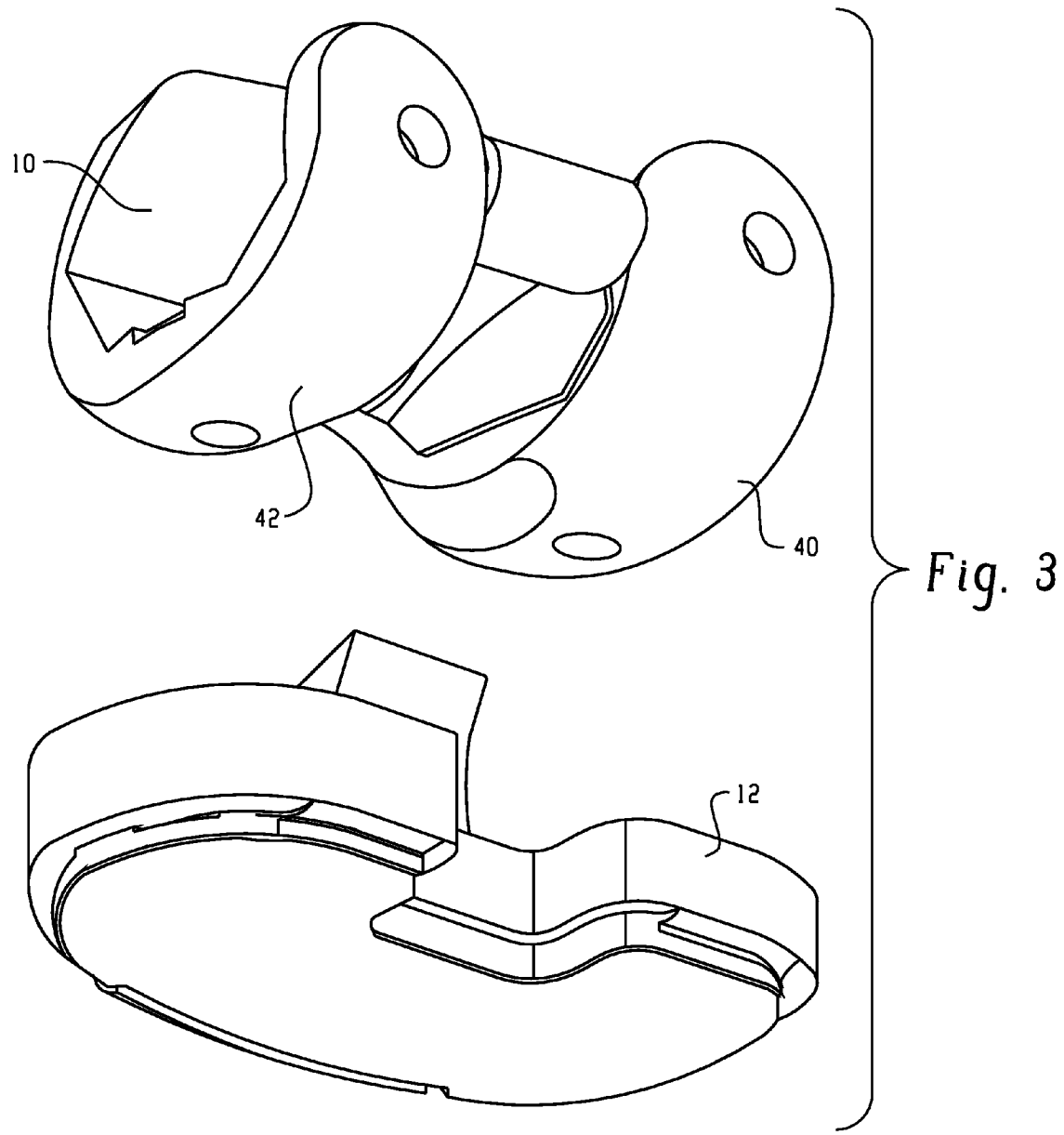
FIG. 3 is another exploded view of the exemplary stereolithography femoral trial and the stereolithography tibial tray insert trial of FIG. 2.

Referencing FIGS. 1-3, several orthopedic stereolithography (SLA) trials 10, 12, 14 are shown that in combination would comprise a trial knee joint orthopedic replacement. As used within the instant disclosure, "trial" refers to a proposed design of a tangible orthopedic implant fabricated to an actual size and shape, but that has not yet received FDA approval and/or is not intended to be implanted permanently. Those skilled in the art are familiar with orthopedic knee joint replacements and knee joint replacement trials that are commonly fabricated from various materials such as, without limitation, polymers, ceramics, and metals. For purposes of explanation only, a permanent knee joint replacement is generically referred to herein as an orthopedic joint replacement, which commonly includes a femoral component 10, a tibial tray insert component 12, and a tibial tray component 14. Nevertheless, it is to be understood that the exemplary methods discussed below are applicable to designing and selecting any other orthopedic joint replacement component such as, without limitation, those components for use in shoulder and hip replacements.

Prior art techniques for developing orthopedic implants typically involve utilization of computer aided design (CAD) software. Typical CAD software allows an orthopedic implant designer to change virtually anything related to the size and shape of the implant. CAD software has evolved to include artificial generation of kinematic data and pressure data based upon an electronic simulation of how the designed orthopedic components will interface with one another during a range of movement. This simulated data is used to narrow the possibilities for a preferred orthopedic design, resulting in several designs typically emerging. At this point in the design process, orthopedic designers construct SLA models/trials of the preferred design elements, usually from plastics. These trials are not for permanent implantation, but are fabricated to show the designers the actual size and shape of the implants before manufacture of the permanent version. It is important to note that the configuration of these prior art SLA models is fixed and that any geometric differences that exist between multiple orthopedic designs mandates fabrication of completely new SLA models. The designers arrive at an optimal design consensus typically without any testing of SLA's in vivo. Rather, the designers agree on the final design and authorize fabrication of the final implant (manufactured out of the final materials), which is ultimately implanted in patients for study under IRB approval. At this point in the design process, some modifications can be made to the permanent design based on the experience of surgeons both intraoperatively and postoperatively, but any such modifications would be very minor.

Prior art design techniques would rarely, if ever, take the various SLA trials, implant them in place of the normal joint, and take the replacement joint through a range of motion. To the extent any SLA trials are taken through a range of motion, only qualitative assessments are made by orthopedic designers and consulting surgeons. Ultimately, one combination of the SLA trials (femoral, tibial tray, tibial tray insert) is selected as the overall best design for the new orthopedic knee system. But such a design approach relies solely on the artificial predictions of the CAD software and qualitative assessments of the designers and surgeons, without ever measuring in vivo pressures exerted by the implants upon one another. In direct contrast, the instant invention uses actual in vivo pressure and kinematic data to design and optimize an orthopedic joint and its corresponding components.

The method of the instant invention may make use of CAD software to initially design one or more fixed orientation orthopedic implants for trialing. Unlike prior art methods, the instant method obtains actual in vivo pressure and kinematic data showing how the trials interact with one another. It should also be understood that other forms of data may be gathered in addition to or in lieu of pressure data such as, without limitation, fluoroscopic data, X-ray data, accelerometer data, vibration data, sound data, and ultrasonic data. In other words, the instant method constructs SLA models/trials of orthopedic components (such as a femoral component, a tibial tray component, and a tibial tray insert component) using CAD software inputs. After the SLA trials have been fabricated, each trial is outfitted with one or more sensors, such as pressure sensor arrays, on those surfaces or embedded within the trials that will physically contact one another.

Figure 4:
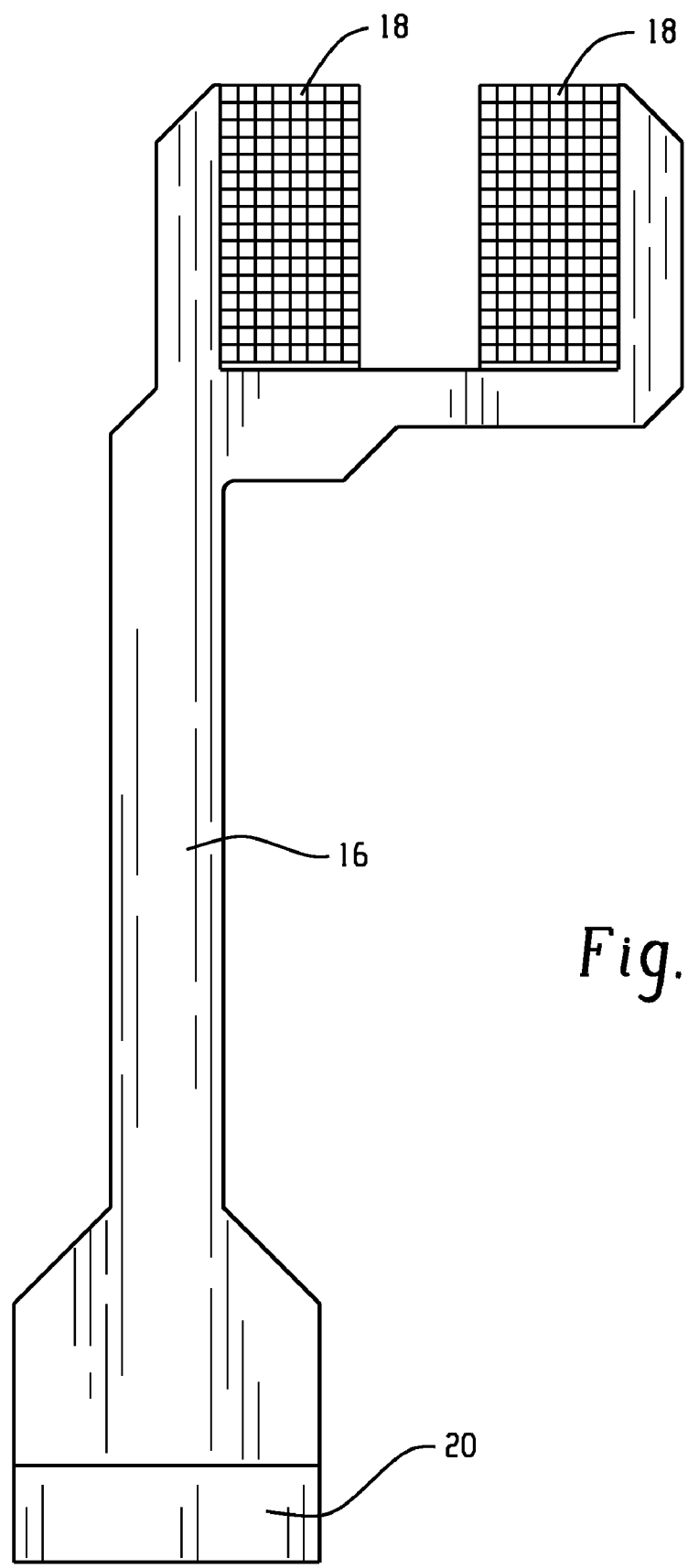
FIG. 4 is an exemplary pressure sensor array for use in the instant invention.

Referring to FIG. 4, an exemplary commercially available pressure sensor array or grid 16 is available from Novel gmbh, Munich, Germany (www.Novel.de). An example of a commercially available grid 16 from Novel gmbh is the S2015 sensor grid that comprises two spaced apart sensor matrices having 16×8 pressure sensors 18. A single connector 20 provides an output data interface from both sensor grids that is adapted for connection to a computer and associated software for transmitting pressure and magnitude data from each sensor on the grid to a visual display associated with the computer.

Figure 5:
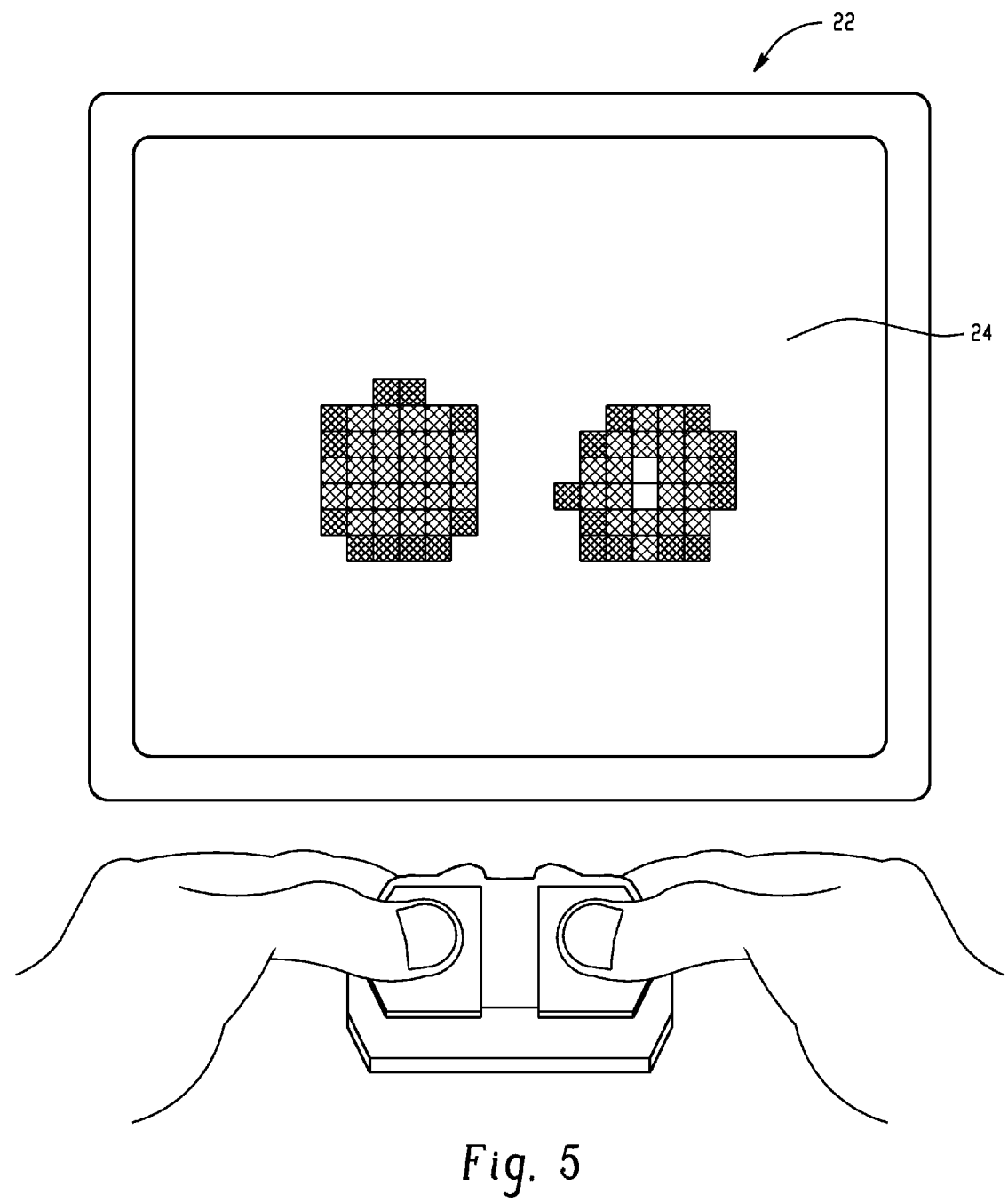
FIG. 5 is a pictorial representation of a computer screen showing how physical pressures, contact areas, magnitudes, and distributions on an exemplary tibial tray insert trial are displayed.

Referencing FIG. 5, a computer 22 includes a software program available from Novel gmbh that is operative to use the data output from each sensor 18 by way of the connector 20 to reproduce a virtual sensor grid on the computer screen 24. This reproduction provides a color-coded visual grid with multiple rectangles corresponding to the sensors. Each rectangle visually represents, in real-time, the magnitude of pressure exerted upon each sensor or adjacent group of sensors by way of color and a numerical read-out. As shown in FIG. 5, each condyle receiver of the tibial tray insert trial 12 includes a corresponding one of the 16×8 pressure sensor arrays 16. Thus, when pressure is applied either or both condyle receivers, the computer screen 24 depicts which sensors are detecting pressures greater than atmospheric pressure (i.e., ambient conditions). In this manner, an observer of the computer screen 24 is able to discern precisely the magnitude and location of pressures exerted upon the tibial tray insert trial 12.

Figure 6:
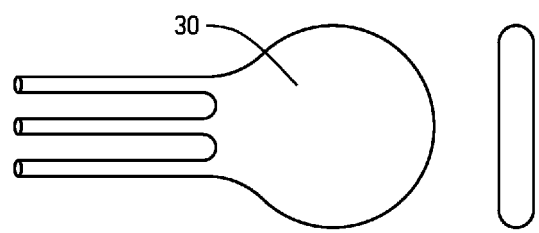
FIG. 6 is an exemplary pressure sensor for use in the instant invention.
Figures 7A, 7B, 7C:
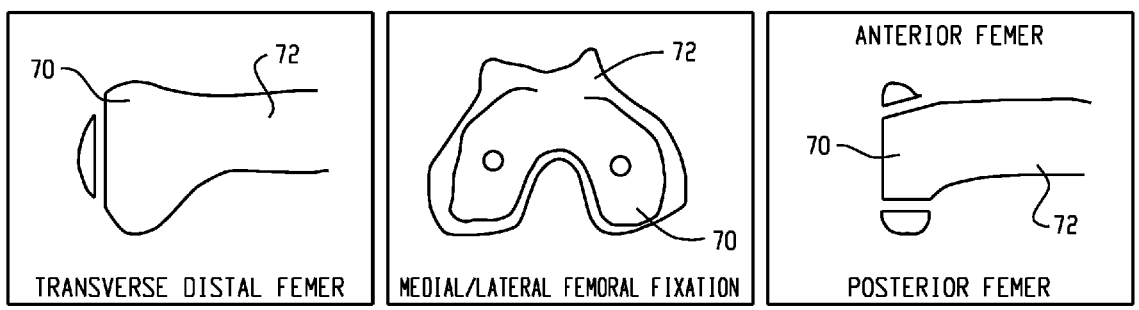

Referring to FIG. 6, another available sensor for use with the instant invention is the Model 060 3-lead miniature pressure transducer 30 available from Precision Measurement Company, Ann Arbor, Mich. (http://www.pmctransducers.com). This transducer is fabricated from stainless steel and provides the availability to measure pressures from zero to two-thousand pounds per square inch. In exemplary form, a series of Model 060 transducers are mounted to a backer material (not shown), to maintain the orientation of the transducers in a predetermined configuration, which is externally mounted to an SLA trial and exposed to sense pressures. In an alternate exemplary embodiment, the Model 060 transducers are embedded within the SLA trials. These predetermined configurations have been matched to the wirings of the transducers to correlate the electrical signal output from the transducer array according to the position and configuration of the transducers. In this manner, one can obtain transducer output signals that are representative of both pressure and position. The output signals are then interpreted by a signal processor and utilized by software to construct a positional spreadsheet that numerically changes in real-time corresponding to the pressures detected by each transducer. As a result, pressure data changes as a function of time and orthopedic implant position are recorded.

Referring back to FIGS. 2 and 3, each femoral trial 10 includes a pair of condyles 40, 42 that engage corresponding condyle receivers 44, 46 associated with the tibial tray insert trial 12. In exemplary form, each condyle 40, 42 is outfitted with a pressure sensor grid 16 (see FIG. 4) from Novel gmbh so that the surfaces of each condyle 40, 42 coming into contact with the condyle receivers 44, 46 of the tibial tray insert trial 12 will include corresponding pressure sensors. In this manner, as the femoral condyles 40, 42 are rotated in vivo through their range of movement with respect to the tibial tray insert trial 12, data is output from the sensor arrays 16 providing quantitative information as to the location and magnitude of pressures exerted upon the femoral trial surfaces. Moreover, by knowing the pressures exerted upon the sensor grids, contact areas can be determined throughout the range of motion. This contact area data may be particularly helpful in identifying areas of the trials that receive heightened stresses and correspondingly designing these areas with reinforcement or changing the design to increase contact areas. In addition to outfitting the femoral condyles with sensors, the tibial tray insert trial 12 may also be outfitted with a pressure sensor array (not shown), where the sensor array covers the condyle receivers 44, 46. But before the orthopedic trials 10, 12, 14 may be implanted and in vivo data taken, several steps must occur to prepare the patient's native tissue.

As discussed in U.S. Pat. No. 4,787,383, the disclosure of which is hereby incorporated by reference, several cuts are made to the native femur and tibia to shape these bones for reception of the orthopedic components. Referencing FIGS. 7A-7E, the distal end 70 of the femur 72 is reshaped by making a series of angled blocked cuts, while the proximal end 74 of the tibia 76 is cut off to leave a generally planar surface exposing the tibial canal (not shown). After these bone cuts have been made, the bones are further prepared to receive the tibial and femoral trials. In exemplary form, these preparations include reaming the tibial canal and predrilling fastener holes within the femur. Those skilled in the art are familiar with the techniques necessary to prepare native tissue to receive orthopedic trials and implants.

Figure 9:
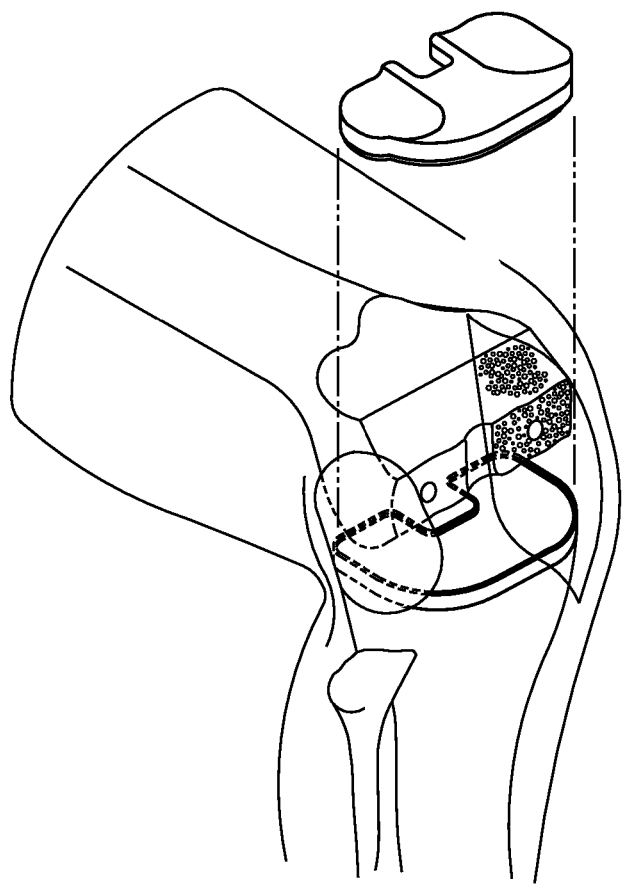
FIG. 9 is an elevated perspective view showing how the tibia tray of FIG. 8 would accept a tibia tray insert.
Figure 10:
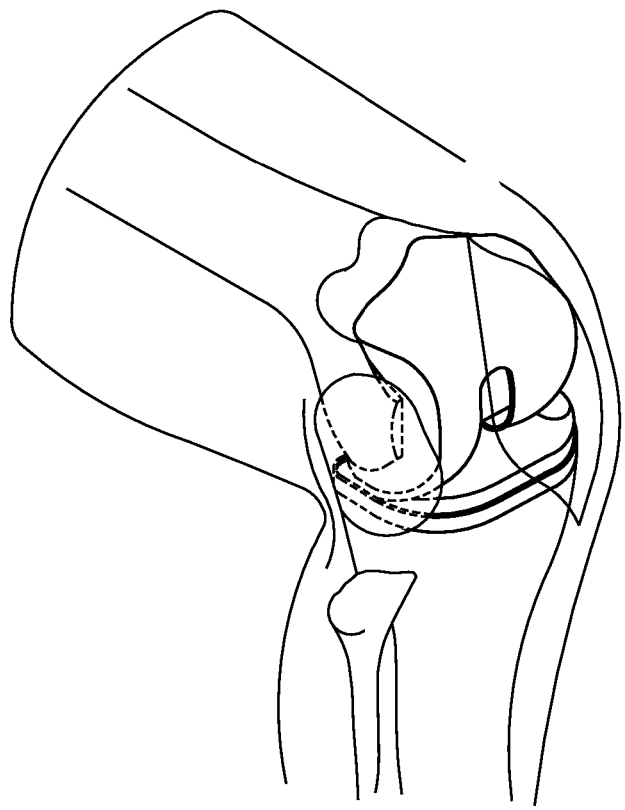
FIG. 10 is an elevated perspective view showing how the patient's femur would receive a femoral implant.
Figure 11:
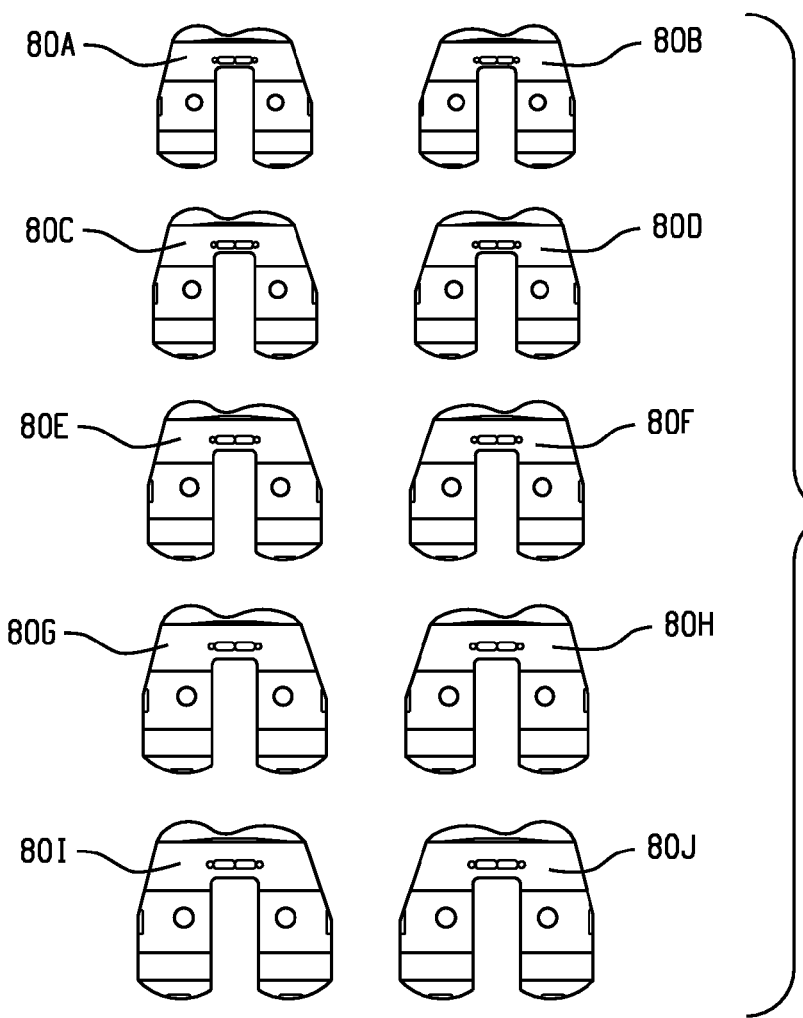
FIG. 11 includes interior views of several complimentary right and left exemplary femoral trials having differing sizes.
Figure 12A:
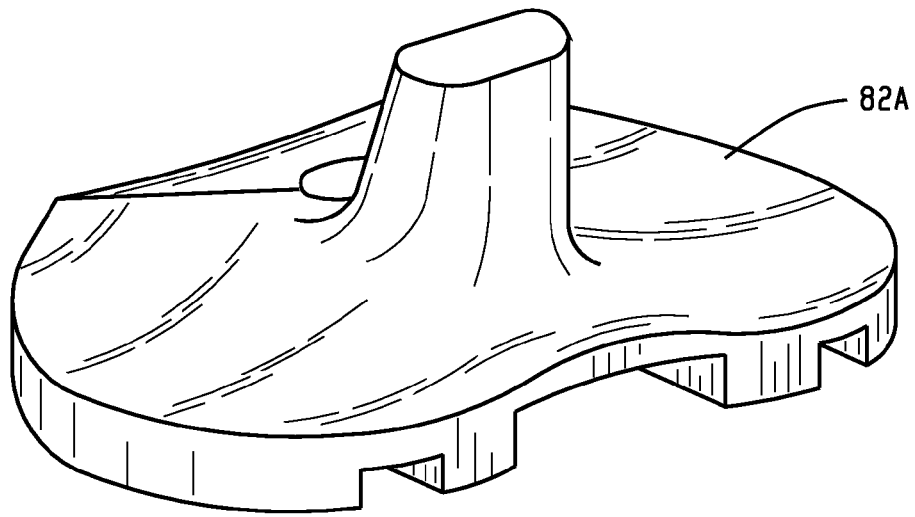
FIGS. 12A-12D are elevated perspective views of several exemplary tibial tray insert trials.
Figure 12B:
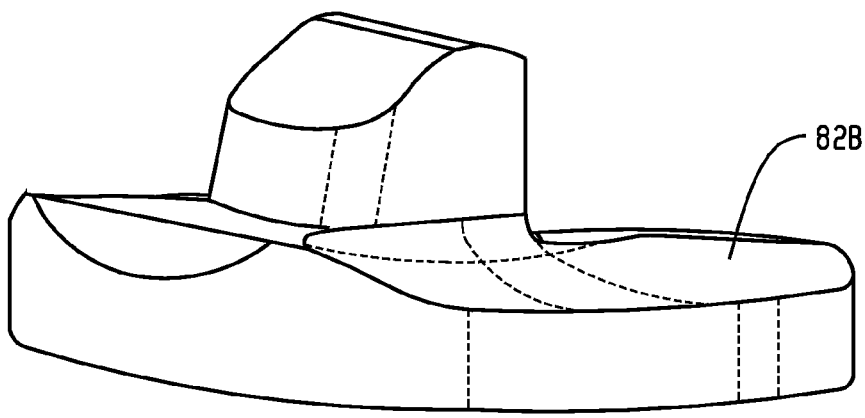
Figure 12C:
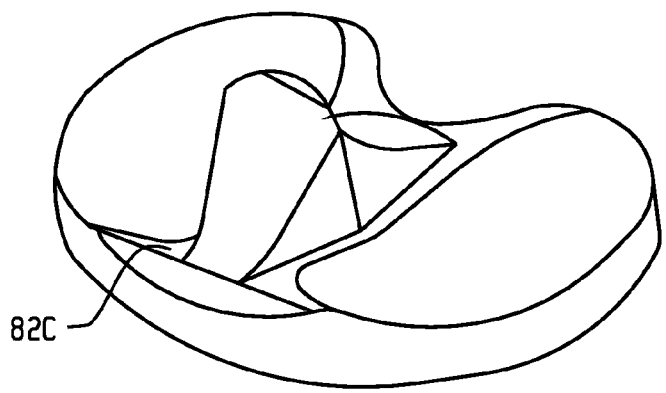
Figure 12D:
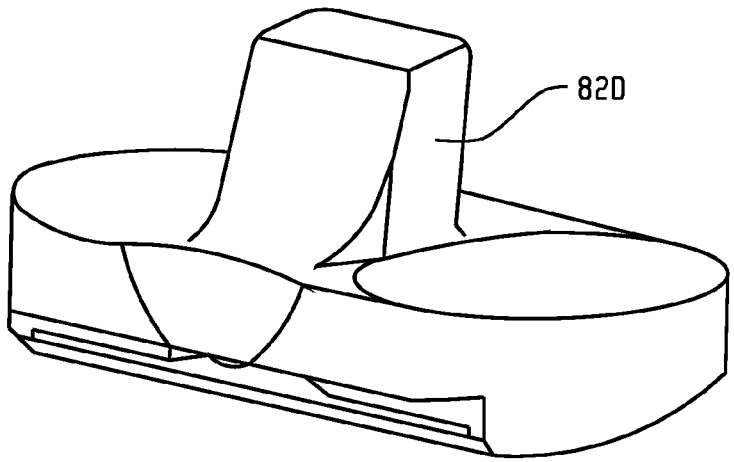

Referring to FIGS. 8-10, after the patient's femur is prepared to accept a femoral trial 80 on the distal end of the femur 82 and the patient's tibia is prepared to accept a tibial tray 84 on the proximal end of the tibia 86, the respective instrumented SLA trials are secured to the femur and tibia.

Referring to FIGS. 11 and 12A-12D, in accordance with the instant invention, the surgeon has at his disposal several different femoral trials 80A-80J, a tibial tray trial 14 (see FIG. 1), and a plurality of tibial tray insert trials 81A-81D, where each trial or selected trials may be outfitted with sensors. Exemplary sensors for use with the trials include, without limitation, pressure sensors, accelerometers, vibration sensors, ultrasonic sensors, and sound sensors.

In exemplary form, after a set of orthopedic trials are implanted, a surgeon takes the orthopedic trials through a range of motion similar to that of a normal knee. As the trial orthopedic knee joint is moved through its range of motion, in vivo sensor data is generated from each of the respective sensor grids associated with the orthopedic trials. This sensor data is useful to determine which SLA trial combination is preferred by looking at: 1) medial and lateral compartment pressure magnitudes—to insure they do not exceed the material properties or values that might increase wear or lead to implant loosening; 2) medial and lateral compartment contact areas throughout the range of motion—to insure they remain comparable to minimize the stresses throughout the range of motion and to avoid known abnormal loading patters such as edge loading or point contact or liftoff (complete loss of contact area); 3) medial and lateral compartment pressure distributions—to insure that normal knee kinematics are occurring (e.g., rollback, internal tibial rotation with flexion, etc) from reviewing the exact orientation of the femoral component relative to the tibial component; and, 4) dynamic pressure magnitude, distribution, and kinematics to be compared to dynamic databases in the computer interface. Exemplary dynamic databases include, without limitation, normal pre-operative kinematic data, normal post-operative kinematic data, abnormal pre-operative kinematic data, and abnormal post-operative kinematic data.

Orthopedic SLA trials can vary in many significant ways. For example, tibial tray insert trials could vary by post location (medial or lateral or anterior of posterior), post orientation, rotation, and shape (height, width, angles), condyle receiver shape (depth, angle, length), tray thickness, and whether the tray is fixed or mobile bearing. Likewise, the femoral trial could vary by the shape of the J-curve, cam location, cam orientation, radii of curvature of the condyles, thickness of the condyles, spacing between the condyles, coronal geometry, and varying the foregoing between the medial and lateral trials. As discussed above, SLA trials include fixed geometric features resulting from their unitary construction. Instead of fabricating and testing a plethora of fixed geometry SLA trials, the instant invention may also make use of reconfigurable trials that allow for geometrical reconfiguration.

Referring to FIGS. 13-16, a reconfigurable tibial tray insert 90 includes an arrangement of orifices 98, with at least one of the orifices 98 to receive a dowel 100 of a corresponding tibial tray insert post 102. The arrangement of orifices 98 allows the position of the post 102 to be changed in between trial implantations to see how changes in the position of the post affect contact pressures and kinematics of the artificial joint. Specifically, the arrangement of orifices 98 include orifices that are centered and offset from the medial-lateral centerline. In addition, one or more of the orifices 98 may be centered or offset from the anterior-posterior centerline. In exemplary form, the orifices 98 are electronically mapped and each orifice is given a specific reference corresponding to its location. For example, the orifice most anterior and lateral is given the designation A, with the anterior-posterior direction contributing a reference letter ("A" for example) that is incremented sequentially from anterior to posterior based upon the distance from the A reference orifice. In addition, the medial-lateral direction contributes a reference number ("1" for example) that is incremented sequentially from medial to lateral based upon the distance from the 1 reference orifice. In this manner, an orifice positioned at the farthest anterior and farthest medial might have a reference A1, while an orifice at the farthest posterior and farthest lateral might have a reference Z26. In other words, the first orifice medial from the A1 orifice is designated A2, while the first orifice posterior from the A1 orifice is designated B1. In the exemplary tibial tray insert trial 90 shown in FIG. 15, the orifices 98 may be designated C13, T13, K7, K19. It should also be understood that in certain circumstances the tibial tray insert 90 will not include a post 102, particularly where a cruciate retaining tray insert is implanted.

Figure 15:
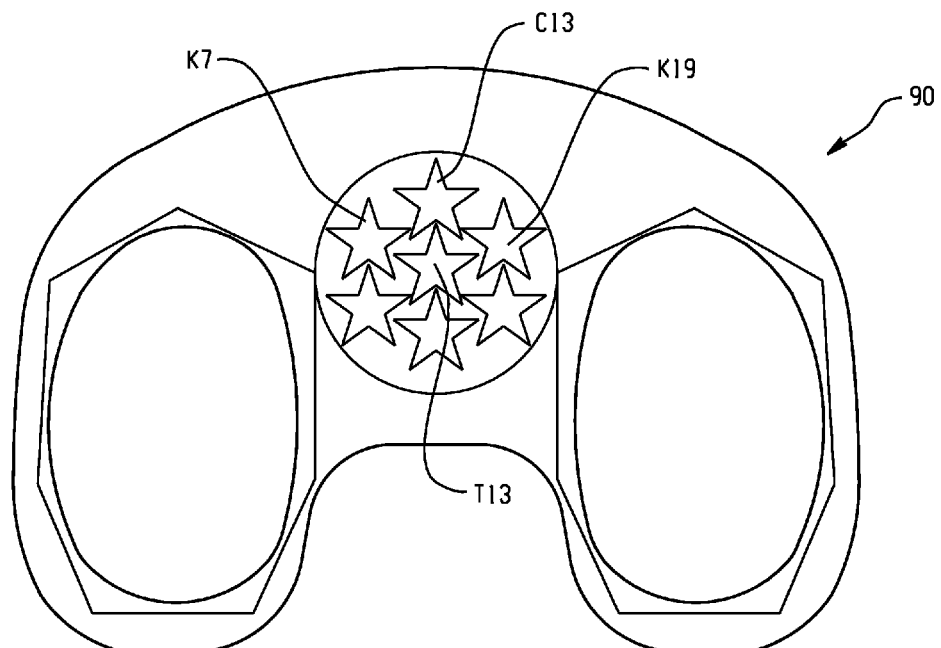
FIG. 15 is an overhead view of an exemplary tibial tray insert trial in accordance with the instant invention.
Figure 16:
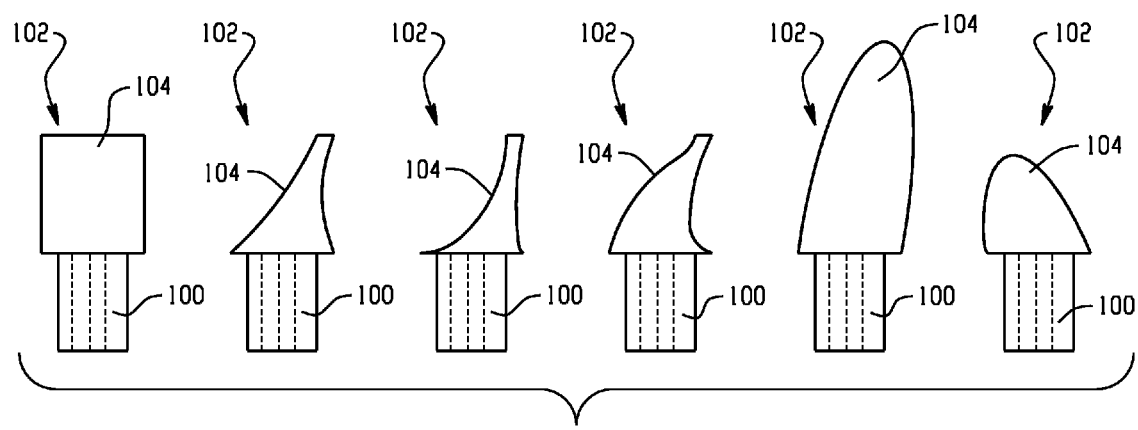
FIG. 16 is a profile view of several exemplary tibial tray insert post trials in accordance with the instant invention.

Referring specifically to FIGS. 15 and 16, a plurality of removable trial posts 102 may be used with the reconfigurable tibial tray insert 90. Each post 102 includes a contoured top 104 attached to a cylindrical dowel 100 that is adapted to be received within one of the orifices 98 of the reconfigurable tibial tray insert 90. Depending upon the preference of the surgeon/physician, the dowel 100 may be locked to inhibit rotation with respect to the tibial tray insert 90, or may be allowed to freely rotate or rotate within a predetermined range. Those skilled in the art will be knowledgeable as to the plethora of devices that one might use to bring about this functionality including, without limitation, set screws. In addition, as will be discussed in more detail below, it is also within the scope of the invention to includes orifices 98 shaped other than cylindrically, as well as dowels shaped other than cylindrically (see FIGS. 15 and 16). In this exemplary line-up, the dowels 100 perpendicularly extend from each contoured top 104. It should be noted, however, that the dowels may be oriented at angles other than ninety degrees and that the dowels may be reconfigurably angled using set screws (not shown) between serial joints (not shown) incorporated within the dowel 100. Those skilled in the art will also understand that shims may be added to the underside of each post to vary the height of the post within a Z-axis. While several exemplary shaped posts 102 are shown, it is to be understood that other exemplary shaped posts could be utilized and all such alternative designed posts fall within the scope and spirit of the present invention.

Figure 17:
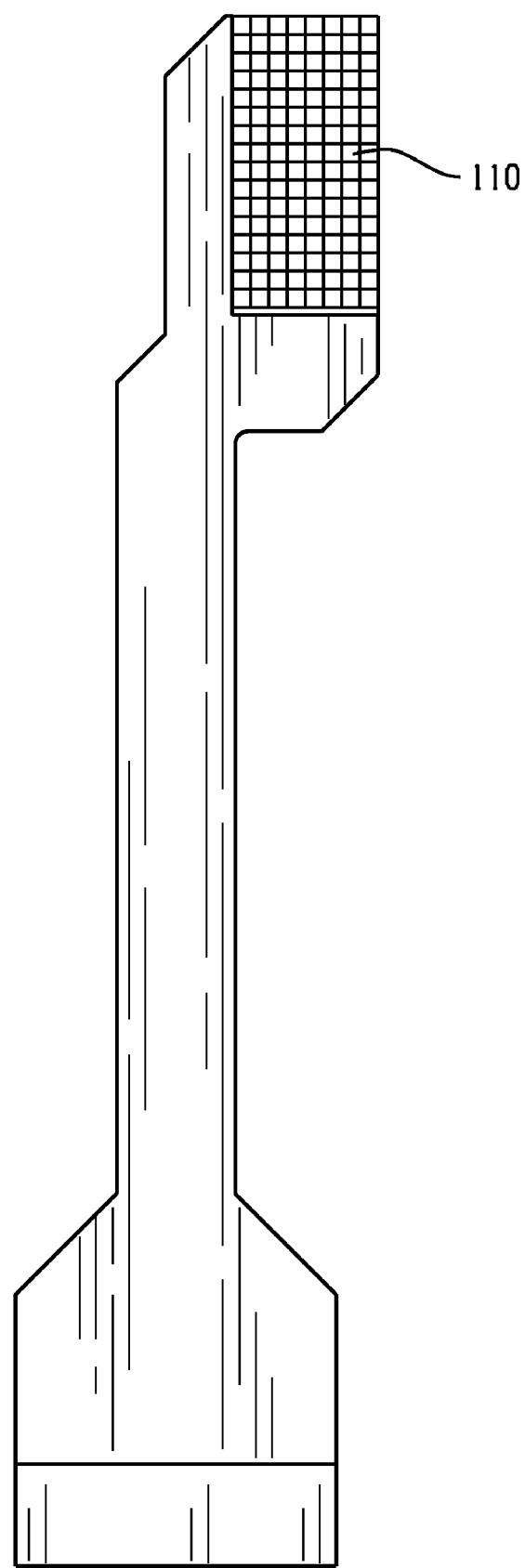
FIG. 17 is an exemplary pressure sensor array for use in the instant invention.
Figure 18:
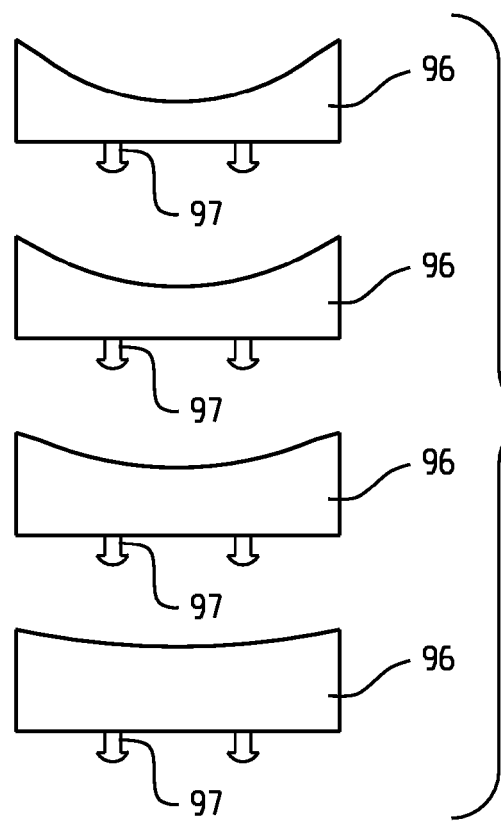
FIG. 18 are frontal views of a series of exemplary condyle receiver inserts for a tibial tray insert trial in accordance with the instant invention.

Referring to FIGS. 16 and 17, each trial post 102 is outfitted with a sensor array 110 so that dynamic pressure data may be generated from contact between the post and the femoral trial. An exemplary sensor array for use with the post trials includes, without limitation, an S2014 pressure sensor array from Novel gmbh (www.Novel.de). Because each orifice 98 of the tibial tray insert trial is identified by a unique identifier, as is each post trial, when a particular post trial 102 is tested in vivo, the location of the post, identification of the post, height of the post, and angle of the post can be easily recorded in conjunction with the pressure data generated by the sensor array 110. In this manner, a surgeon can choose from various trial posts 102 and learn how changes in the shape of the contoured top 104, changes in the angle of the top (by way of the angled dowel 100), changes in the height of the contoured top 104, and changes in the location of the trial post 102 affect pressures exerted within the artificial joint and joint kinematics. Likewise, each trial post 102 may be outfitted one or more of the following sensors or arrays of sensors: accelerometers, vibration sensors, ultrasonic sensors, and sound sensors. In addition, or in the alternative, the patients natural tissue may be outfitted (internally or externally) with one or more of the following sensors or arrays of sensors to gather data during the course of tissue ranges of movement: accelerometers, vibration sensors, ultrasonic sensors, and sound sensors.

It is also within the scope of the invention to include fluoroscopic data acquisition and/or X-ray data acquisition when repositioning orthopedic implants or trials in vivo. Those skilled in the art are familiar with fluoroscopy and X-rays, as well as devices utilized to take and record fluoroscopic images and X-ray images. Specifically, the fluoroscopic images and X-ray images are, in exemplary from, taken from a profile view of a joint and oriented on a split screen so that a surgeon and/or joint designer, for example, can see the movement of the joint in vivo in addition to pressure and positional measurements taken in a time matching display. Accordingly, any anomalies evident from either display can be evaluated with a second set of data at approximately the same time as the anomaly. In other words, numerical data from one or more sensors is time matched with pictorial data to allow concurrent qualitative and quantitative analysis.

Referencing FIG. 15, it is also within the scope of the invention to include orifices 98 within the tibial tray insert trial 90 that are not cylindrical in shape. By way of example, and not limitation, an orifice 98 may be shaped to receive a spline dowel (not shown). In such a circumstance, the rotational position of the post trial could be varied, but fixed for purposes of in vivo data gathering. Other orifices 98 could exhibit a hexagonal shape to receive a corresponding hexagonal dowel. In addition, orifices 98 could be star-shaped (see FIG. 15), rectangular, or triangular to receive a star-shaped (see FIG. 16), rectangular, or triangular dowel 100. Those skilled in the art will readily understand the variations in dowel shape and corresponding cavity shape that will allow rotational position adjustability of the post trial 102.

Referring to FIGS. 13-16 and 18, the reconfigurable tibial tray insert 90 includes a right side bay 92 and a left side bay 94 that receive corresponding condyle receiver inserts 96. In exemplary form, a plurality of condyle receiver inserts 96 are removably mounted to the reconfigurable tibial tray insert 90 using one or more prongs 97 that are received within cavities 99 formed within the tray insert 90. Each receiver insert 96 embodies a different shape to enable the surgeon to see how shape of the condyle receivers affects joint pressures and kinematics. Each of the stock condyle receiver inserts 96 may be manipulated using filament shims (not shown) that are adhered to the condyle receivers. Exemplary filament shims include, without limitation plastics, metals and/or ceramics. In this fashion, the condyle receivers may be readily reconfigured to change the depth, angle, and length without requiring fabrication of a completely new tibial tray trial. After the condyle receivers have been built up in the selected areas, presuming this is done at all, a sensor grid may be applied to the surfaces of the condyle receivers to be contacted by the femoral condyles. In this manner, the sensors associated with the condyle receivers 96 will provide output data as to the location and magnitude of pressures exerted between the trials during in vivo joint range of motion.

By using the above reconfigurable tibial tray insert 90, a series of condyle receiver inserts 96 may be fabricated having various geometries (e.g., coronal and sagittal) to provide interchangeability for quick exchange of condyle receivers. For example, a first exemplary condyle receiver insert may have a deep groove that includes an arcuate posterior segment and a linear sloped posterior segment. Obviously, those skilled in the art will readily understand the various design alternatives one might conceive for the shape of a condyle receiver, which could be separately fabricated ahead of time or on the fly for ready insertion into the tibial tray insert trial 90.

Figure 13:
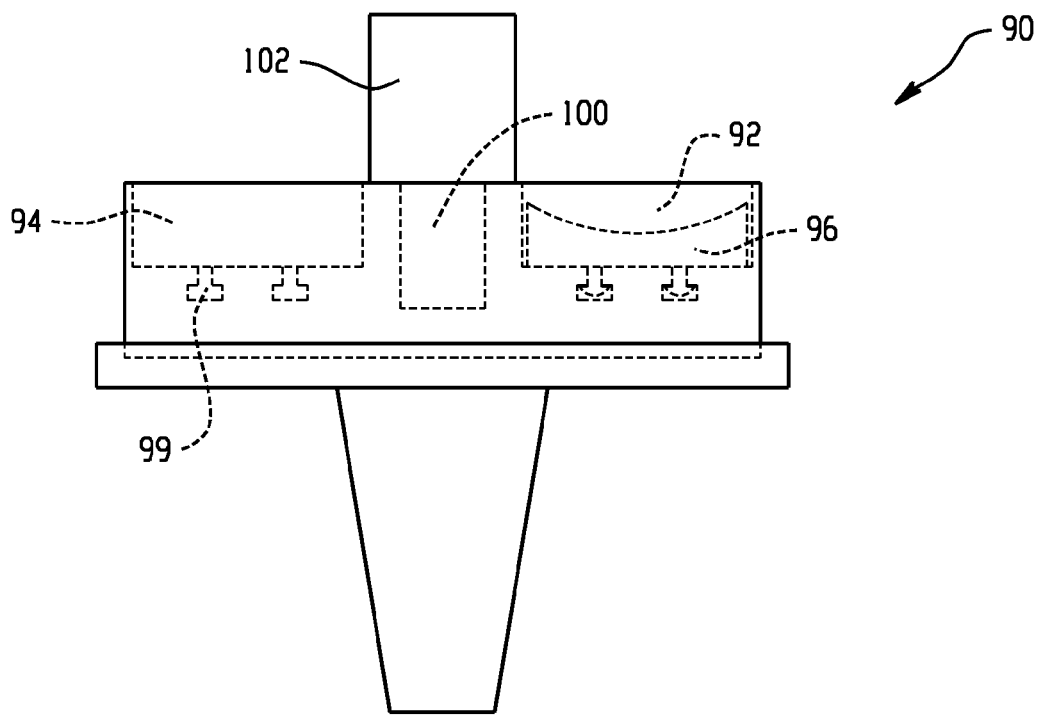
FIG. 13 is a frontal view of an exemplary tibial tray insert trial and tibial tray trail in accordance with the instant invention.
Figure 14:
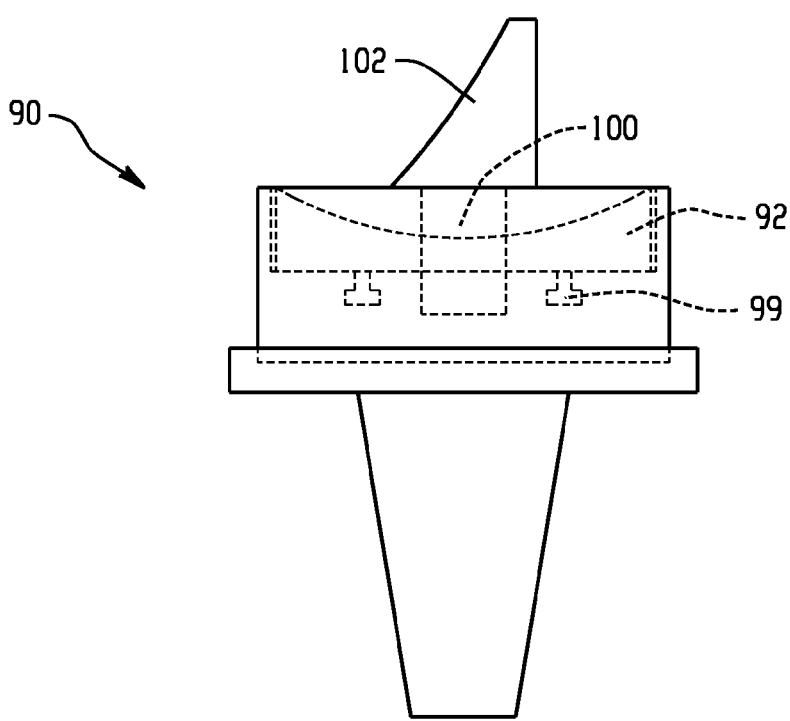
FIG. 14 is a profile view of the exemplary tibial tray insert trial and tibial tray trail of FIG. 13.
Figure 19:
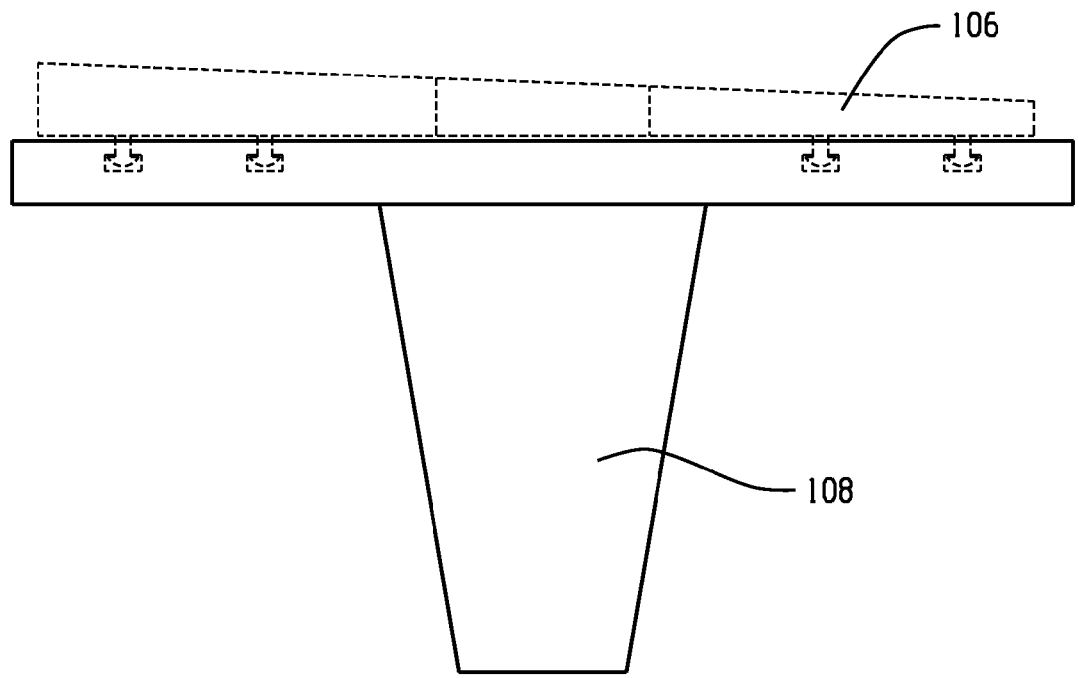
FIG. 19 is a frontal view of an exemplary tibial tray trial, including tibial shim shown in phantom, in accordance with the instant invention.
Figure 20:
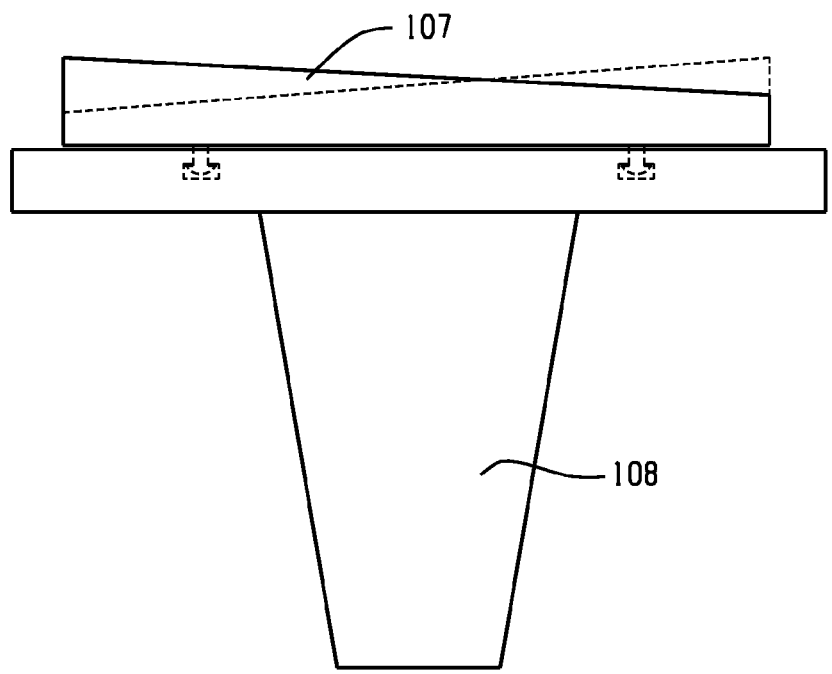
FIG. 20 is a profile view of an exemplary tibial tray trial including tibial shims in accordance with the instant invention.
Figure 21:
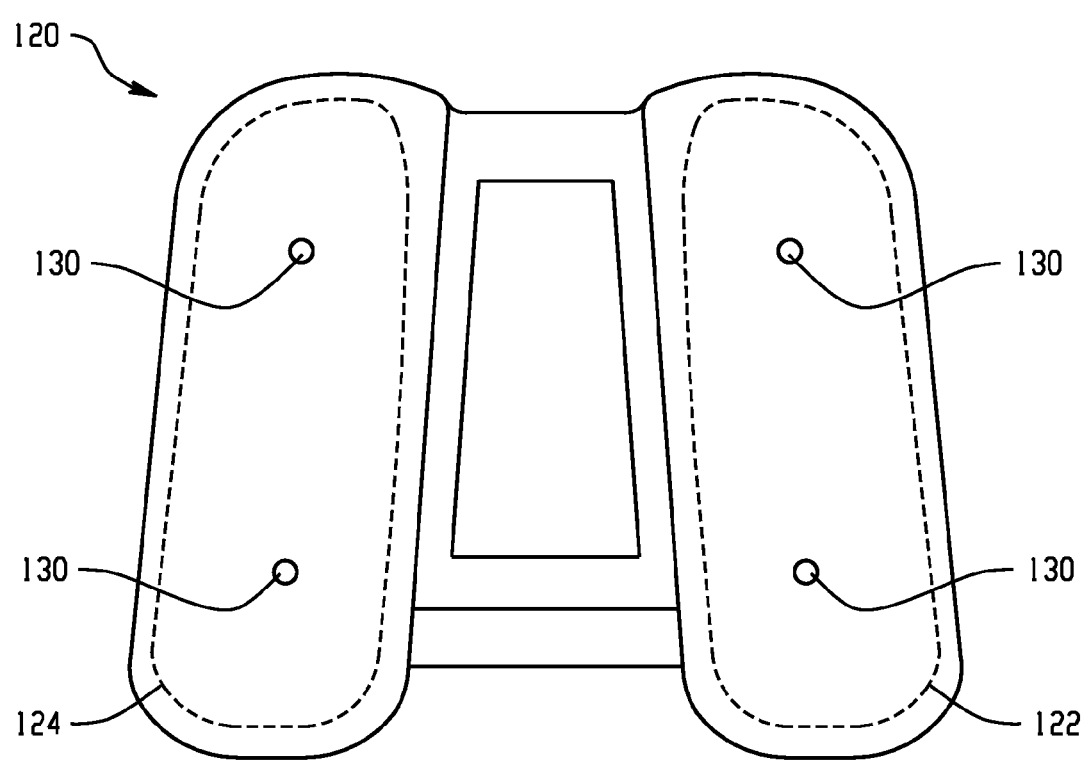
FIG. 21 is a distal view of an exemplary femoral trial in accordance with the instant invention.
Figure 22:
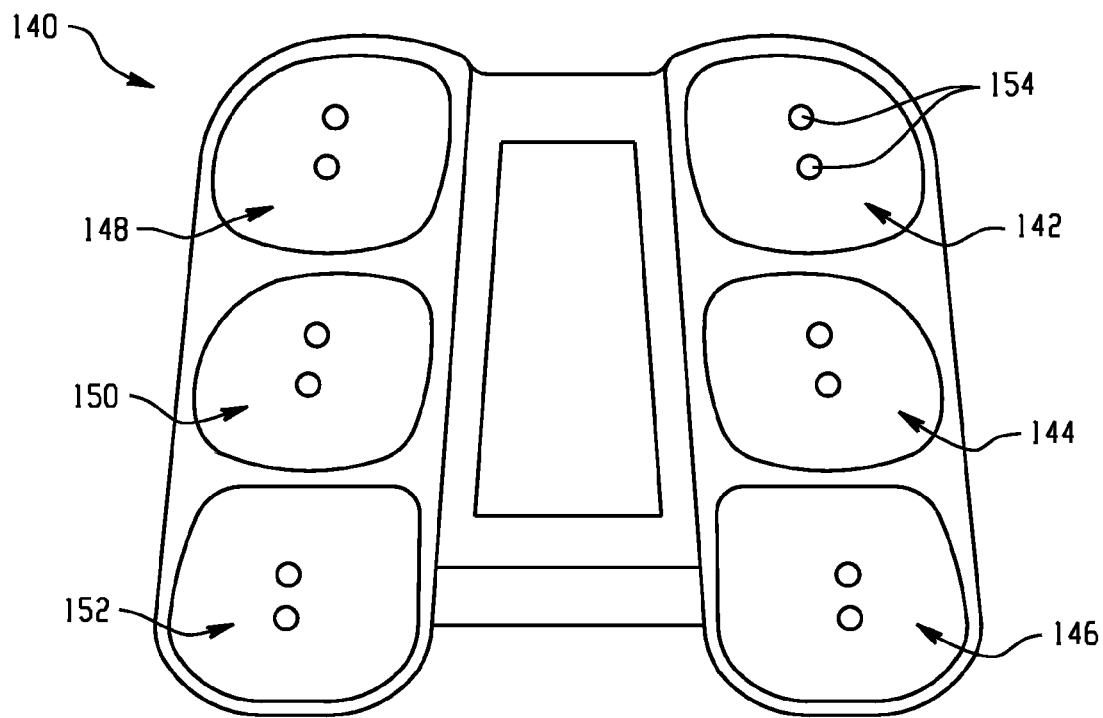
FIG. 22 is a profile view the femoral trial of FIG. 21, with a pair of condyle inserts.
Figure 23:
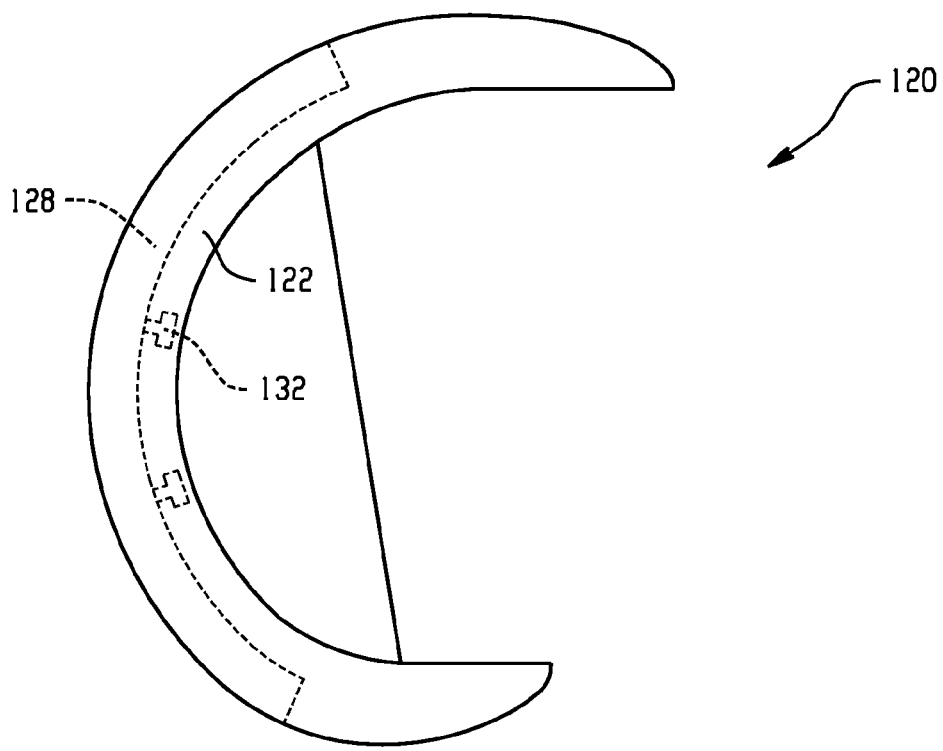
FIG. 23 is a profile view the femoral trial of FIG. 21, with a different pair of condyle inserts.
Figure 24:
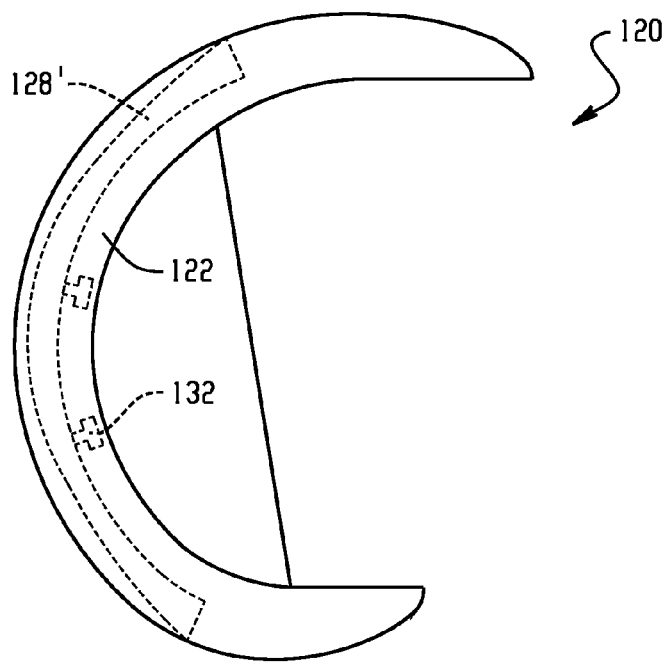
FIG. 24 is a profile view the exemplary condyle insert of FIG. 22.

Referencing FIGS. 19 and 20, the reconfigurable tibial tray insert trial 90 may be mounted to tibial tray shims 106, 107 mounted to the tibial tray 108 to vary the orientation of the tray insert 90 (see FIG. 13). The 106, 107 shims might also be made to vary in thickness from anterior to posterior or to vary the slope as well as medial to lateral. A plethora of tray shims may be manufactured at predetermined thicknesses, where one or more of the shims are stackable to provide the ability to use multiple shims to increase the thickness of the tibial tray insert trial for in vivo testing. Each shim would include its own unique identifier so that one would be able to quickly discern the thickness of the tibial tray insert trial without requiring measuring.

Referring to FIGS. 21-25, a first reconfigurable femoral trial 120 includes a right condyle cutout 122 and a left condyle cutout 124, where each cutout 122, 124 may include a cavity, projection, or other feature adapted to interact with a condyle insert 128, 128' to mount the condyle insert 128 to the femoral trial 120. In this first exemplary femoral trial 120, the right condyle cutout 122 and the left condyle cutout 124 each include a pair of cavities 130 that each receive a corresponding projection 132 of a condyle insert 128.

Two exemplary condyle inserts 128, 128' are shown that exhibit variances in size and shape. By way of example, and not limitation, a first condyle insert 128 exhibits a first J-curve, while a second exemplary condyle insert 128' exhibits a second J-curve. Obviously, those skilled in the art will readily understand the various design alternatives one might conceive for the shape of a condyle, which would be separately fabricated ahead of time for ready insertion into the overall femoral trial. These condyle inserts 128, 128' are removably mounted to the condyle cutouts 122, 124 to construct the femoral trial 120. Presuming the surgeon is satisfied with the size and shape of the condyles, each condyle may be outfitted with an exterior sensor array 110 (see e.g., FIG. 17) so that dynamic pressure data may be generated from contact between the condyles and corresponding condyle receivers of the tibial tray insert trial. An exemplary sensor array for use with the condyles includes, without limitation, an S2014 sensor array from Novel gmbh (www.Novel.de). In exemplary form, the sensor array is oriented onto each condyle using a reference mark (not shown) on the condyle to standardize the position of the sensor array with respect to the condyles. In this manner, data from the sensor array may be correlated to positional data to show precisely where on the condyles pressures were detected and in what magnitude during in vivo range of motion of the artificial joint.

Figure 26:
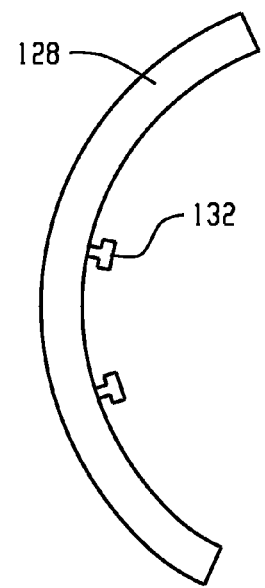
FIG. 26 is a distal view of another exemplary femoral trial in accordance with the instant invention.
Figure 25:
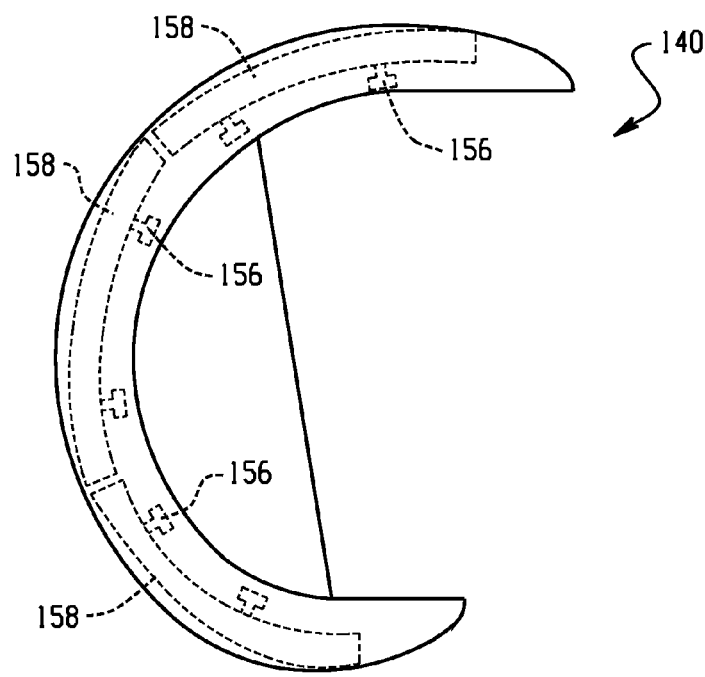
FIG. 25 is a profile view the exemplary condyle insert of FIG. 23.
Figure 27:
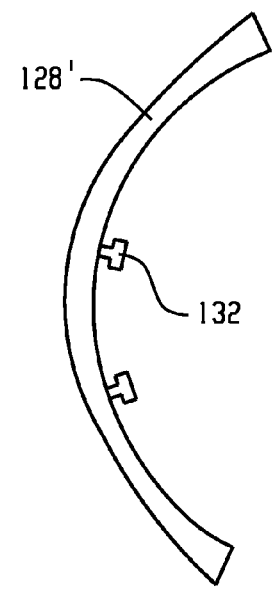
FIG. 27 is a profile view the femoral trial of FIG. 26, with a series of condyle inserts.
Figure 28:
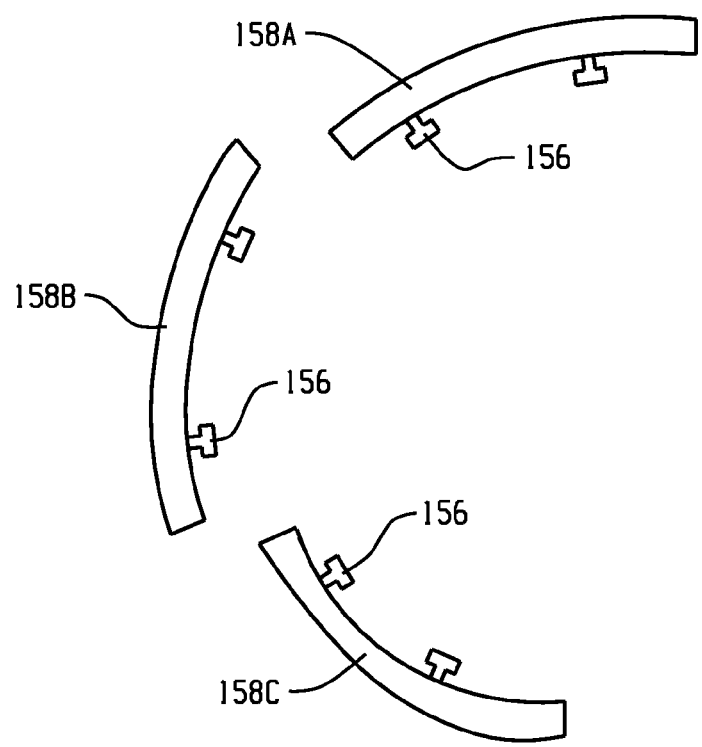
FIG. 28 is a profile view the exemplary condyle inserts of FIG. 26.

Referring to FIGS. 26-28, a second reconfigurable femoral trial 140 includes multiple medial condyle cutouts 142, 144, 146 and lateral condyle cutouts 148, 150, 152 where each cutout includes a pair of cavities 154 is adapted to receive a corresponding projection 156 of a condyle insert 158. The exemplary condyle inserts 158 (including inserts 158A, 158B, and 158C) may exhibit variances in size and shape. By way of example, and not limitation, an anterior condyle 158A insert may exhibit a slightly curved contour, while a more posterior condyle insert 158C may exhibit a more pronounced curvature, particular at toward the posterior end. Obviously, those skilled in the art will readily understand the various design alternatives one might conceive for the shape of a condyle, which would be separately fabricated ahead of time for ready insertion into the overall femoral trial 140. These condyle inserts 128 are removably mounted to the condyle cutouts 142-152 to construct the femoral trial 140. Presuming the surgeon is satisfied with the size and shape of the condyles, each condyle may be outfitted with a sensor array 110 (see FIG. 17) so that dynamic pressure data may be generated from contact between the condyles and corresponding condyle receivers of the tibial tray insert trial. An exemplary sensor array for use with the condyles includes, without limitation, an S2014 sensor array from Novel gmbh (www.Novel.de). In exemplary form, the sensor array is oriented onto each condyle using a reference mark (not shown) on the condyle to standardize the position of the sensor array with respect to the condyles. In this manner, data from the sensor array may be correlated to positional data to show precisely where on the condyles pressures were detected and in what magnitude during in vivo range of motion of the artificial joint.

Alternatively, the shape of the stock condyles may be manipulated using filament shims (not shown). In exemplary form, the condyles may be readily reconfigured to change the width, J-curve shape, and angle without requiring fabrication of a completely new femoral trial. After the shape of the condyles reach a desired shape using the filament shims, an array of pressure sensors is adhered to the exterior of the condyles where the condyles will contact the tibial tray insert trial during the range of movement of the femoral trial. As discussed above, an exemplary sensor array for use with the condyles includes, without limitation, an S2014 sensor array from Novel gmbh (www.Novel.de).

Figure 29:
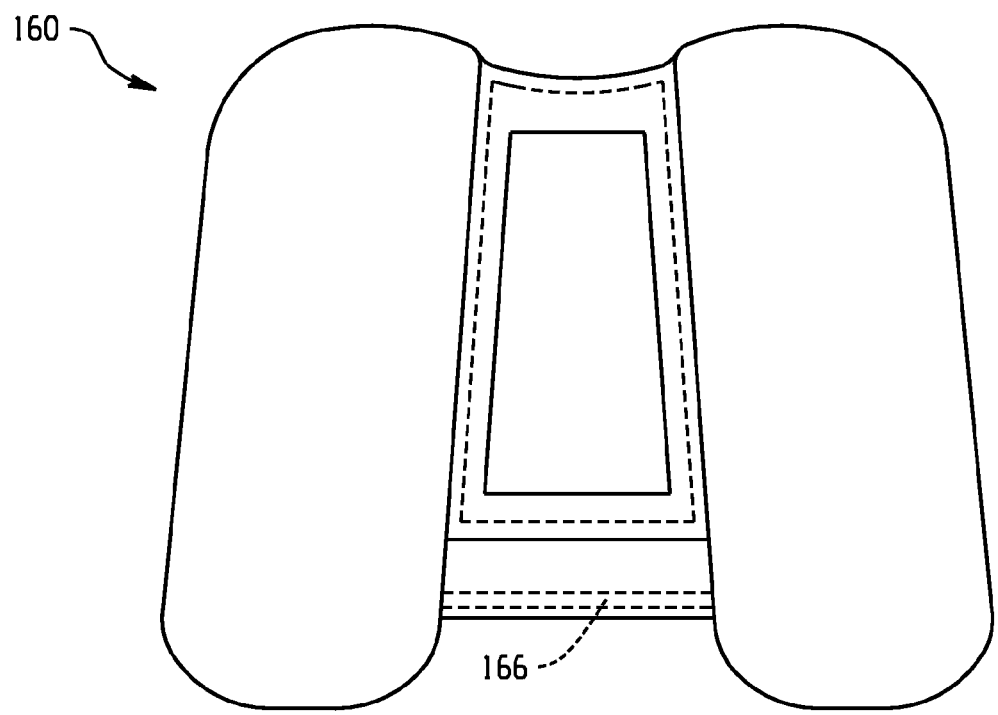
FIG. 29 is a frontal view of an exemplary femoral trial.
Figure 30:
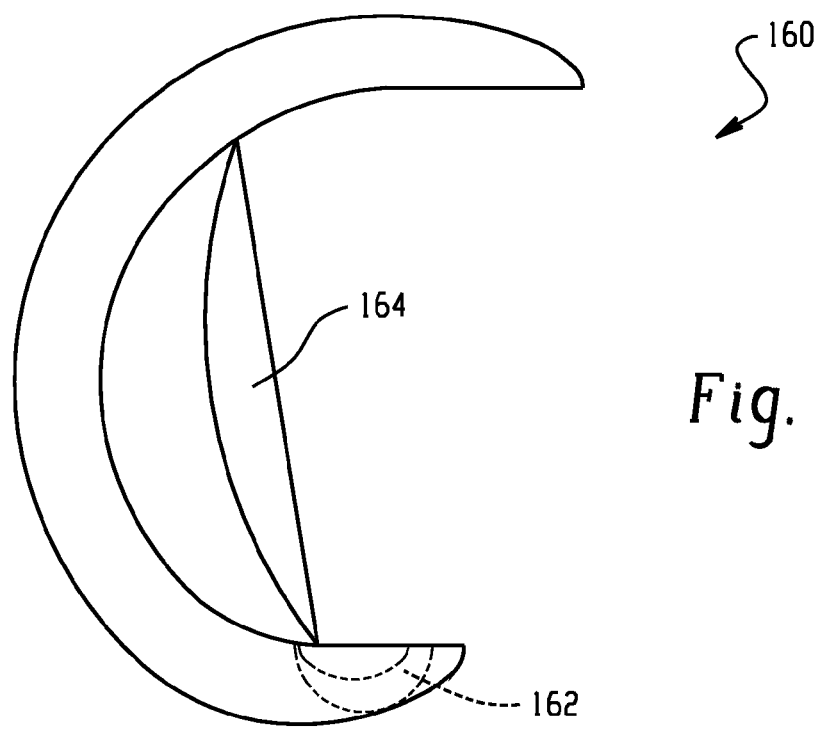
FIG. 30 is a profile view of the exemplary full femoral trial of FIG. 29.
Figure 31:
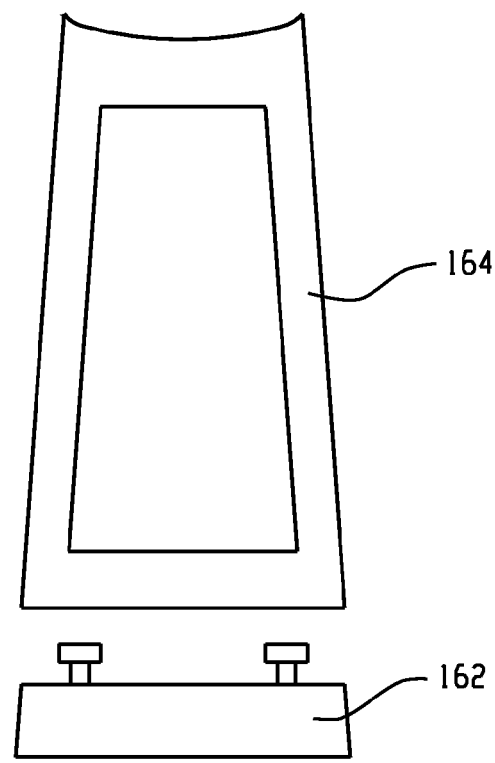
FIG. 31 is a frontal view of the exemplary full femoral cam and box of FIGS. 29 and 30.
Figure 32:
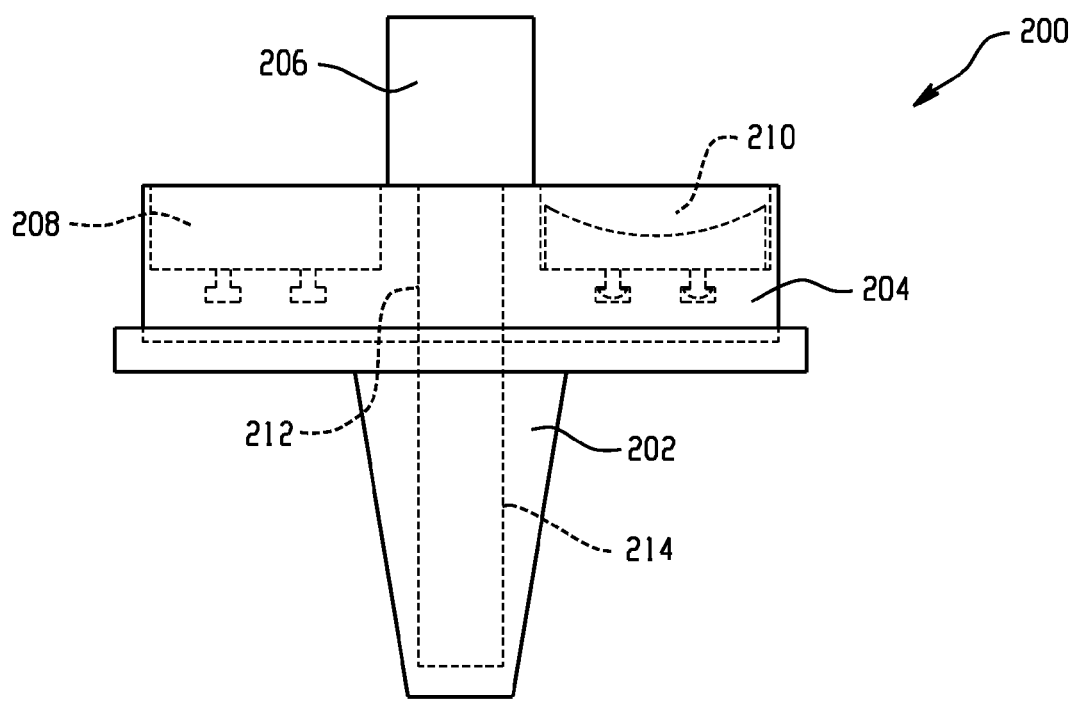
FIG. 32 is a frontal view of an exemplary tibial tray insert trial and tibial tray trial, where the tibial tray insert post is rotatable.
Figure 33:
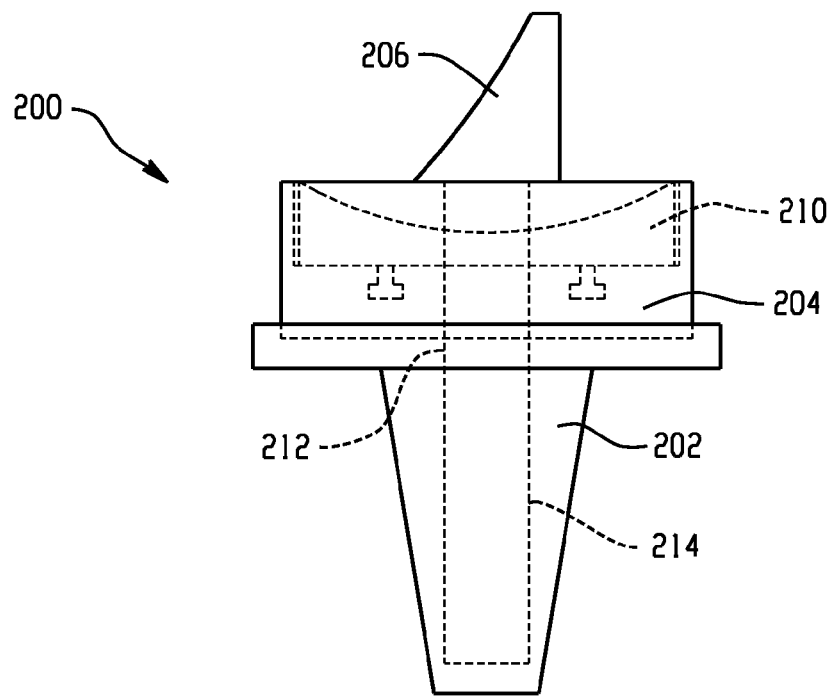
FIG. 33 is a profile view of an exemplary tibial tray insert trial and tibial tray trial, where the tibial tray insert post is rotatable.
Figure 34:
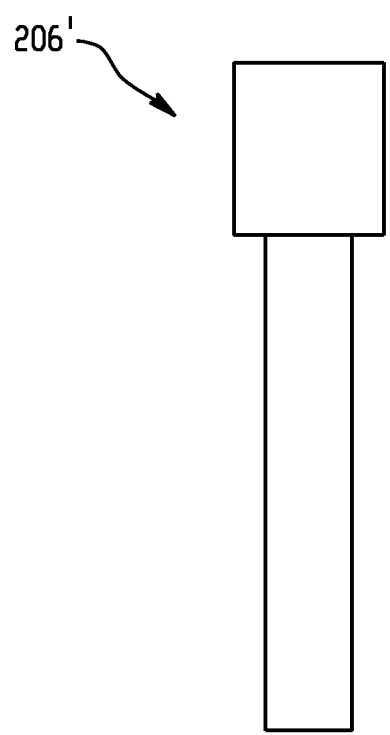
FIGS. 34 and 35 are exemplary tibial tray insert posts for use with the tibial tray insert trials in FIGS. 32 and 33.
Figure 35:
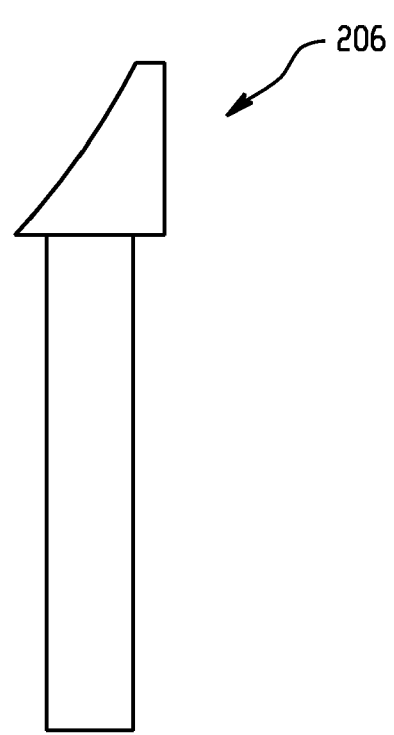
Figure 36:
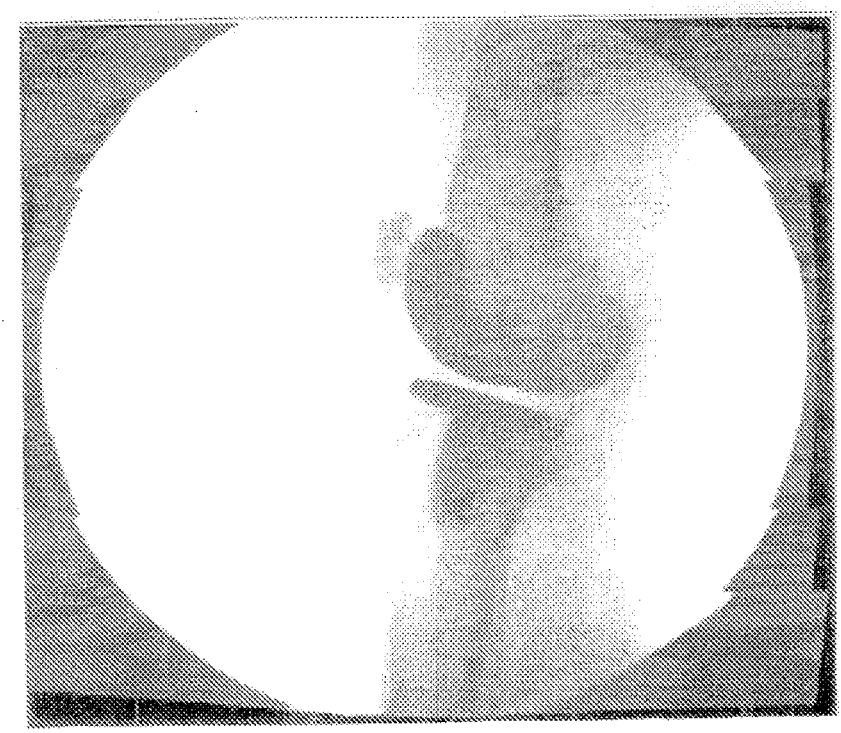
FIGS. 36-39 are profile fluoroscopic images of an orthopedic knee implant at discrete points through a knee bend or range of motion.
Figure 37:
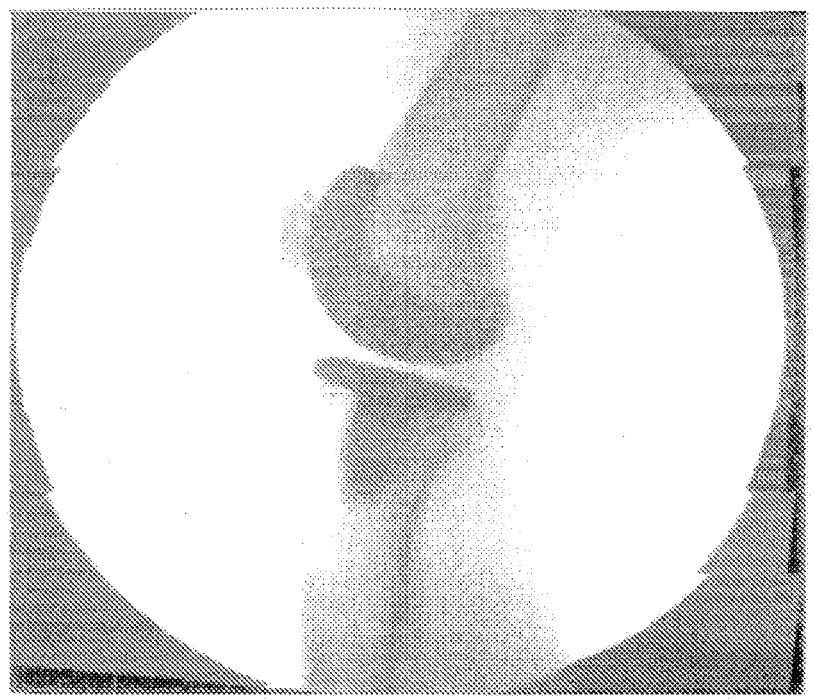
Figure 38:
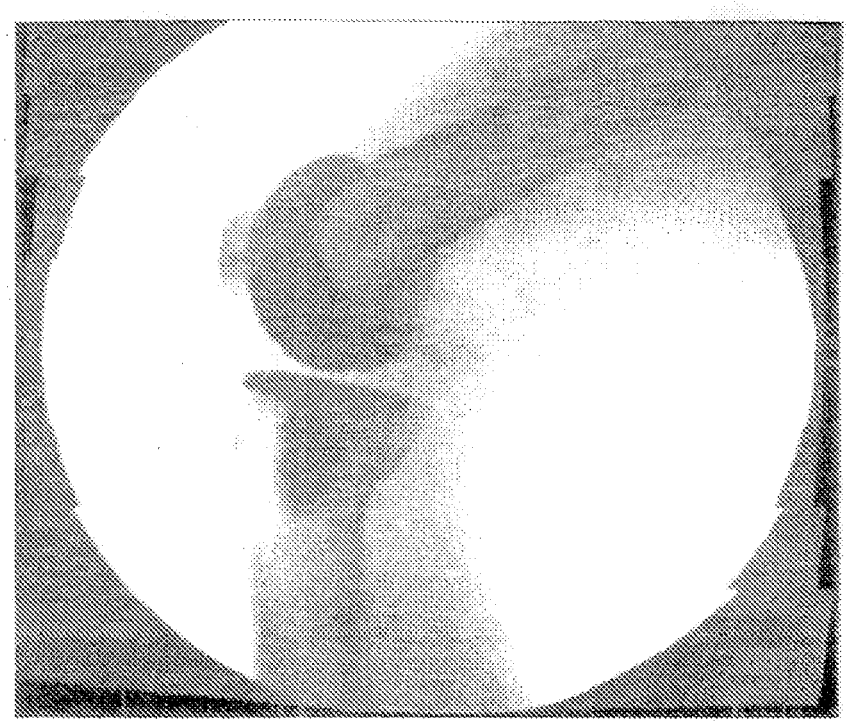
Figure 39:
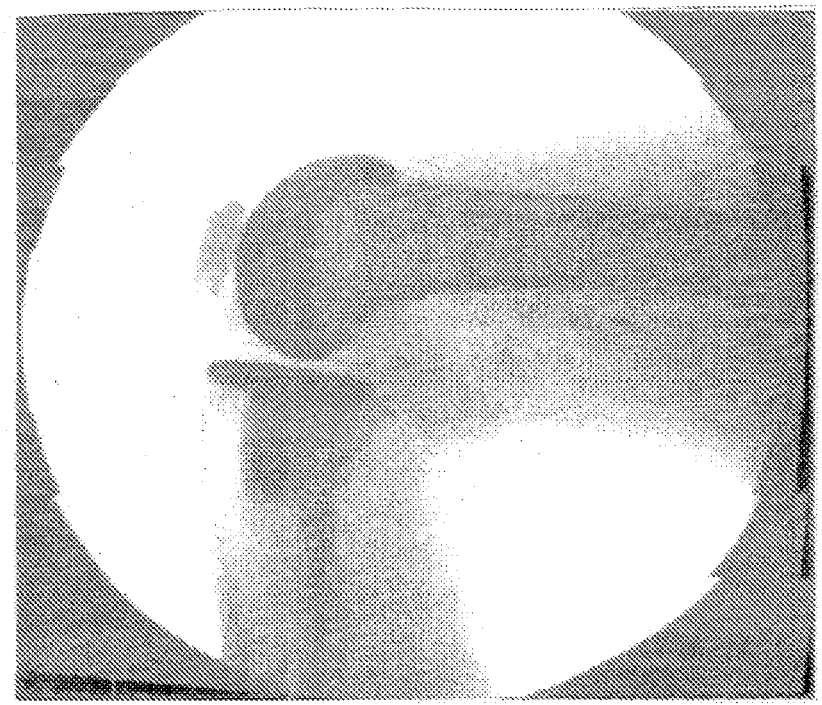

Referring to FIGS. 29-31, it is also within the scope of the invention to allow a femoral trial 160 to accept various trial inserts 162, 164. In exemplary form, a plurality of cam trial inserts 162 with differing shapes and sizes are available to mount to the generic tunnel 166 to provide cams at various positions along the J-curve. In a preferred embodiment, each cam trial insert 162 includes its own unique identification and each mounting location of the generic tunnel includes its own unique identification. Accordingly, one can vary the size of the cam, the shape of the cam, as well as its mounting position to the tunnel 166, and track its interactions with the tibial trial post to determine aspects such as, without limitation, how the location of the cam effects rollback of the femoral trial. Each cam trial insert 162 is outfitted with a pressure sensor array so that contact with the post generates dynamic sensor data during in vivo testing of the trials. As discussed above, an exemplary sensor array for use with the cam trial insert 140 includes, without limitation, an S2014 sensor array from Novel gmbh (www.Novel.de). Thus, the reconfigurable femoral trial 160 provides shape and positional variance of a cam trial insert 162 along substantially the entire J-curve. Because the locations of the mounting points for the cam trial insert 162 on the tunnel 166 are predetermined and each cam trial insert 162 includes its own unique identification, when a particular cam trial insert is tested in vivo, the location of the cam and its identification can be easily recorded to correlate the pressure data taken as a function of location. Similarly, a plurality of box trial inserts 164 with differing shapes and sizes are available to mount to the femoral trial 160 to provide boxes having predetermined configurations (i.e., widths, lengths, depth, curvature 167, etc.). In a preferred embodiment, each box trial insert 164 includes its own unique identification. Accordingly, one can vary the size of the box and the shape of the box and track its interactions with the tibial trial post to determine aspects such as, without limitation, how the location of the box effects rollback of the femoral trial. Each box trial insert 164 may be outfitted with a pressure sensor array so that contact with the post generates dynamic sensor data during in vivo testing of the trials. Because each box trial insert 164 includes its own unique identification, when a particular box trial insert is tested in vivo, its identification (and associated unique geometric features) can be easily recorded to correlate the pressure data taken as a function of location.

Referencing FIGS. 32-35, the principles of the instant invention are also applicable to trails having mobile bearing features. In exemplary form, a mobile bearing tibial trial 200 includes a tibial tray trial 202, a tibial tray insert trial 204, and a tibial post trial 206. The exemplary tibial tray insert trial includes a pair of bays 208 adapted to receive inserts 210 providing a particular shape for each condyle receiver. A through hole 212 is provided in the tibial tray insert trial to accommodate insertion and rotation of the tibial post 206. A cavity 214 is provided within the tibial tray to accommodate a distal end of the tibial post 206. The orientation of the hole 212, as well as the orientation of the cavity 214, allow the post 206 to rotate 360 degrees. In exemplary form, sensors (not shown) are mounted to the exposed portions of the condyle receiver inserts 210 and the exposed portion of the post 206 that provide pressure feedback when the trial 200 is implanted and put through a range of motion. In like manner, the tibial post 106 may be exchanged for another post 106' exhibiting different geometric features, implanted, and in vivo data taken to discern how changes in geometry affect pressures, kinematics, and wear characteristics. This same concept is also applicable to the condyle receiver inserts 210.

For purposes of brevity, only a single exemplary mobile bearing example is discussed herein. From the instant disclosure, however, those skilled in the art will readily understand the applicability of these principles to other mobile bearing prosthetic components. In this manner, the instant invention is not limited to mobile bearing trials for use with total knee arthroplasty. For example, the instant invention may be applied to hip and shoulder arthroplasty procedures to facilitate design and selection of the appropriate prosthetic on a patient-specific or class-specific basis.

The ability to intraoperatively adjust the geometric configuration of the trials in order to gather sensor data from those trials outfitted with sensors, while using the same femoral and tibial bone cuts, provides the orthopedic designer (by way of the surgeon) with the ability to ascertain how specific femoral and tibial trial design modifications effect the kinematics of the orthopedic joint and pressures exerted upon the orthopedic joint elements during in vivo range of movement. For example, by changing the position of the post of the tibial tray insert, the designer is able to see how this change impacts knee kinematics and contact points between the femoral component and tibial tray insert. Exemplary repositioning of the tibial tray insert post position includes movement in the anterior-posterior and the medial-lateral directions and rotation.

While the foregoing orthopedic trials have been explained in terms of sensor arrays or grids that are external to the orthopedic trials, it is also within the scope of the invention to utilize sensors that are internal to the orthopedic trials. Internal sensors and sensor arrays have been disclosed in co-pending U.S. patent application Ser. No. 11/890,307, entitled "SMART JOINT IMPLANT SENSORS," the disclosure of which is hereby incorporated by reference. While the foregoing incorporated disclosure addresses internal sensors for permanent orthopedic implants, the same teachings could be easily applied to orthopedic trials.

As discussed above, the tibial tray insert trial and femoral trial may be instrumented with sensors to measure relative pressure magnitudes and distributions of the relative tibiofemoral contact positions. It is also within the scope of the invention to utilize other sensors such as, without limitation, accelerometers, vibration sensors, ultrasonic sensors, and sound sensors. The data generated by the sensor arrays associated with the trials is dynamic, thereby generating data set across the entire range of movement of the orthopedic trials reflecting both the position of the pressures and the magnitude of the pressures. In this manner, the data may reflect any changes in the location and magnitude of the pressures exerted upon the orthopedic trials as a function of change in position of the trials along their range of motion. In addition, this dynamic data can be manipulated to generate tibiofemoral kinematic data used to construct a computer 3-D model showing how the trial components were moving with respect to one another intraoperatively. When pressure sensors are utilized, the central contact point for each pressure distribution is determined for each compartment and then the relative positions of the femoral and tibial implants with respect to one anther are determined by the computer interface in real time during range of motion trialing. Each data set (sensor pressure data including magnitude as a function of position & kinematic data) may then be compared to a database having similar data sets for normal knees, as well as analogous data sets for patients already having a total knee arthroplasty procedure.

In exemplary form, the comparison of patient data occurs electronically within an artificial neural network ("ANN"). ANN may be comprised of software or a combination of software and hardware. For example, ANN may include a plurality of simple processors each connected by communication channels carrying data. Whether ANN comprises only software or a combination of software and hardware, the software includes a training rule to correlate the importance of certain connections between data. This training rule may be hard programmed or soft programmed by the programmer when correlating certain data and giving the correlated data a particular grade on a fixed scale.

Exemplary data from patient cases to be correlated might include, without limitation: (1) orthopedic implant data for particular designs; (2) patient specific data such as race, gender, height, weight, and age; (3) in vivo orthopedic pressure and/or kinematic data from trials taken during a range of movement; (4) pre-operative (from modeling and finite element testing) and post-operative kinematic data for the particular orthopedic implant; and (5) limb mechanical axis data; (6) arthropometric patient specific data (from pre-operative x-rays and/or CT or MRI 3-D reconstructions) showing the size and shape of the original tibia and femur bones with the desire to match this morphology with the implants (so as not to oversize or undersize or stuff gaps with more implant than bone than anatomically present or intraoperatively removed). By correlating the patient-specific data with data from other patient cases having a positive to exceptional outcome, ANN is able to compare the aforementioned data prospectively (with the exception of post-operative kinematic data) for each patient and predict whether a preexisting orthopedic design would be preferred. ANN also provides guidance to a designer looking for potential design modifications to current designs as well as a starting point for unique orthopedic implant designs.

By way of example, and not limitation, ANN records how specific trial modifications affect pressure magnitudes, distributions, contact areas, and kinematics. In exemplary form, a surgeon implants a series of trial combinations and takes each combination through its range of motion, with ANN recording the results. While the surgeon is contemplating further combinations of trials, ANN provides predictive feedback to the surgeon suggesting which of the possible combinations of trials would be advantageous to try. Alternatively, ANN suggests to the surgeon areas of possible modification and the extent of the modification when using reconfigurable trials. In this manner, ANN reduces the number of trialings needed to arrive at an optimal or preferred design.

Referring to FIG. 36-39, development of normal knee kinematic databases may be accomplished by subjecting a number of patients to a fluoroscope or X-ray machine while performing deep knee bends or passive range of motion that reproduces trialing. The resulting output from the fluoroscope and X-ray machine provides data showing how the tibia moves with respect to the femur during a deep knee bend and passive range of motion. Generally speaking, as the normal knee is moved from an extended position to a bent position, the distal portion of the femur rolls with respect to the proximal portion of the tibia so that the contact point between the femur and tibial actually moves anterior-to-posterior. In addition, both condyles of the normal knee rotate laterally as the knee is bent (tibia internally rotates with flexion). Simply put, fluoroscopic data and X-ray data from normal knees provides a dynamic database showing kinematic movement of the knee joint over its normal range of motion. In addition, each normal patient data set may include additional information on the patient's gender, age, race, weight, etc. in order to facilitate ready classification and more accurate comparisons with in vivo orthopedic trial data. It is envisioned that orthopedic implants could be designed specifically for each patient, but it is also within the scope of the invention to design more generic implants that might be classified using gender, age, race, and/or weight.

A comparison of the in vivo (i.e., intraoperative) trial data and patient data from the database may be carried out by a human or may be automated by a computer program. When automated, a computer program compares the intraoperative trial data, and possibly the trial kinematic data, to a series of data sets taken from patients with normal knees and/or earlier patients having a total knee arthroplasty (TKA) procedure. For those patients having a TKA procedure, intraoperative data was taken using trials outfitted with pressure sensors that matched the permanent orthopedic implant. Each patient data set was data taken intraoperatively using trials outfitted with pressure sensors to measure the contact pressures and generate data as to the magnitude, location and distribution and contact area of the pressures when the trials were put through a range of motion. Follow-up data was taken on each patient so that the intraoperative data is supplemented with post-operative data. Generally, on the order of a few months after TKA, fluoroscopic data and/or X-ray data was taken after surgery of the actual implants through a range of movement. This fluoroscopic data is dynamic data and allows one to construct a 3-D representation of the actual implant to determine such things as whether abnormal condylar lift off is occurring, whether the translation occurring between the tibial and femoral components are normal such that the normal tibial internal rotation with flexion is occurring (25 degrees is normal from 0-125 degrees), normal posterior roll-back is occurring with flexion as present in the normal knee: patellofemoral interactions are normal (patella tracking normally): whether in mobile bearing TKA the rotation with flexion (25 degrees is normal from 0-125) is occurring at the tibial insert undersurface (normal) or at the main articulation (abnormal). Using this comparison of sensor and kinematic data, an optimal orthopedic design could be derived for a given patient, and after multiple optimal configurations are determined an optimal design for different patients could be ascertained (best design for male, best design for female, best design for obese, etc).

After an optimal orthopedic design has been chosen and proved from in vivo data in accordance with the instant invention, prior art techniques for fabricating orthopedic implants may be followed. Alternatively, the instant method envisions fabricating orthopedic implants in a substantially real-time basis. To do so, the surgeon would implant a plurality of trials and gather in vivo data. This data would then be compared to a database in substantially real-time to discern which trial provided the best kinematic and pressure results. The surgeon would choose which orthopedic trials provided the patient with the best fit and accordingly forward fabrication instructions to a rapid manufacturing machine. Exemplary rapid manufacturing machines include, without limitation, the Sinterstation HiQ Series SLS System available from 3D Systems Corporation, Rock Hill, S.C. (www.3dsystems.com). Thereafter, the end orthopedic implant would be rapid manufactured based upon the fixed data already programmed for each trial. In other words, each trial is preprogrammed into the rapid manufacturing machine so that upon receiving the appropriate signal, the rapid manufacturing machine would fabricate the orthopedic implant.

Advantageously, if the surgeon were using the reconfigurable trials of the instant invention, the opportunity would exist for a completely custom orthopedic implant. The surgeon would experiment with certain configurations of the respective trial components and take in vivo data on each configuration. Obviously, experience of the surgeon plays a significant role in which combinations of configurations are chosen based upon the anatomy of the patient. The computer interface with its experience from prior cases could also help suggest modular combination that optimize function. After the surgeon is satisfied that a preferred configuration has been obtained, the surgeon would record the particulars of the trials and have each orthopedic implant rapid manufactured. As discussed previously, when using a reconfigurable trial, the shape of each trial component (such as the tibial post trial) is given a unique identifier that allows a computer to build a virtual 3D model of the permanent orthopedic implant that is sent to the rapid manufacturing machine for fabrication.

It is also within the scope of the invention for the surgeon to finalize the orientation of the elements of a reconfigurable trial and then have the trial laser scanned. The output data from the laser scan is used to generate a virtual 3D model that is sent onto the rapid manufacturing machine for fabrication of the permanent orthopedic implant. An exemplary laser scanner for scanning the reconfigurable trial includes the Surveyor RE-Series 3D laser scanners commercially available from Laser Design, Inc., Minneapolis, Minn. (www.laserdesign.com).

It is also within the scope of the invention to use new imaging technologies, such as ultrasound imaging, and x-ray or fluoroscopy imaging to create a 3D bone model The created bone model can be registered in real space with the actual bone. Trial implants can be place on the real bone such that the implants and the bone can be taken though a range of motion then tracked using known optical imaging techniques. Exemplary tracking methods are disclosed in U.S. Patent Publication Nos. 20060293582A1; US20060173268A1; and US20050261571A1.

Information gathered from tracking the bone can be compared to a database of kinematic or other clinically significant information to make determinations about different implants, different implant brands, or different implant designs. For example, after a first effort with implant trials a surgeon may decide to use a different brand or size of medical implant. Alternatively, engineers may use information gathered from the comparison to make design determinations regarding implants as described herein.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of designing and selecting an orthopedic implant design comprising: fabricating an orthopedic implant;
including sensors on an articulating surface of the orthopedic implant;
implanting the orthopedic implant into a patient;
taking the orthopedic implant through a range of motion to generate in vivo kinematic data; and
making adjustments to the design of the orthopedic implant in view of the in vivo kinematic data.

2. A method of designing and selecting an orthopedic implant design comprising:
implanting, in series, a plurality of orthopedic implants into a patient, where each orthopedic implant includes at least one sensor sensing on at least a portion of an articulating surface of each of the plurality of orthopedic implants;
taking each of the plurality of orthopedic implants through a range of motion to generate in vivo kinematic data from the at least one sensor; and
prioritizing the plurality of orthopedic implants in view of the in vivo kinematic data.

3. A method of designing and selecting an orthopedic implant design comprising;
implanting, in series, a plurality of orthopedic implants into a patient, where each orthopedic implant includes at least one kinematic sensor;
taking each of the plurality of orthopedic implants through a range of motion to generate in vivo kinematic data from the at least one sensor; and
modifying a design of at least one of the plurality of orthopedic implants in view of the in vivo kinematic data.

4. A method of designing and selecting an orthopedic implant design comprising:
implanting an orthopedic implant into a patient, where the orthopedic implant includes at least one kinematic sensor;
taking the orthopedic implant through a range of motion to generate in vivo kinematic data from the at least one kinematic sensor; and
modifying a design of the orthopedic implant in view of the in vivo kinematic data.

5. A method of designing and selecting an orthopedic implant design comprising:
implanting an orthopedic implant into a patient, where the orthopedic implant includes at least one kinematic sensor;
taking the orthopedic implant through a range of motion to generate in vivo kinematic data from the at least one sensor;
removing the orthopedic implant;
reconfiguring the orthopedic implant to change its shape;
implanting the reconfigured orthopedic implant into the patient, where the reconfigured orthopedic implant includes at least one kinematic sensor;
taking the reconfigured orthopedic implant through a range of motion to generate in vivo kinematic data from the at least one sensor; and
modifying a design of the orthopedic implant in view of the in vivo kinematic data.

6. A method of designing and selecting an orthopedic implant design comprising:
implanting an orthopedic implant into a patient, where the orthopedic implant includes at least one sensor sensing conditions on at least a portion of a bearing surface;
taking the orthopedic implant through a range of motion to generate in vivo sensor data from the at least one sensor indicative of kinematics;
removing the orthopedic implant;
reconfiguring the orthopedic implant to change its shape;
implanting the reconfigured orthopedic implant into the patient, where the reconfigured orthopedic implant includes at least one sensor sensing conditions on at least a portion of a bearing surface of the orthopedic implant;
taking the reconfigured orthopedic implant through a range of motion to generate in vivo sensor data from the at least one sensor indicative of kinematics; and
prioritizing, between the orthopedic implant and the reconfigured orthopedic implant in view of the in vivo sensor data.

7. A method of designing and selecting an orthopedic implant design comprising:
 implanting a first orthopedic implant into a patient, where the first orthopedic implant includes at least one sensor detecting surface pressure on an articulating surface of the first orthopedic implant;
 taking the first orthopedic implant through a range of motion to generate in vivo sensor data from the at least one sensor;
 removing the orthopedic implant;
 reconfiguring the first orthopedic implant to change its configuration;
 implanting the reconfigured orthopedic implant into the patient, where the reconfigured orthopedic implant includes at least one sensor detecting surface pressure on an articulating surface of the reconfigured orthopedic implant;
 taking the reconfigured orthopedic implant through a range of motion to generate in vivo sensor data from the at least one sensor; and
 selecting a final orthopedic implant design in view of the in vivo sensor data.

8. A method of designing, selecting, and fabricating an orthopedic implant comprising:
 implanting an orthopedic implant into a patient, where the orthopedic implant includes at least one kinematic sensor;
 taking the orthopedic implant through a range of motion to generate in vivo kinematic data from the at least one kinematic sensor;
 removing the orthopedic implant;
 reconfiguring the orthopedic implant to change its shape;
 implanting the reconfigured orthopedic implant into the patient, where the reconfigured orthopedic implant includes at least one kinematic sensor;
 taking the reconfigured orthopedic implant through a range of motion to generate in vivo kinematic data from the at least one kinematic sensor;
 selecting between the orthopedic implant and the reconfigured orthopedic implant in view of the in vivo kinematic data; and
 rapid manufacturing a final orthopedic implant in view of the in vivo kinematic data.

9. A method of designing an orthopedic implant, comprising the steps of:
 a. creating a 3D patient specific bone model using a computer running bone model software;
 b. registering an actual patient bone with the bone model using a computer running registration software;
 c. providing a database of orthopedic implant designs;
 d. selecting an orthopedic implant from the database of implant designs;
 e. providing a database of joint kinematics;
 f. applying the selected implant to the patient specific bone model using a computer running, implant design software;
 g. taking the orthopedic implant applied to the patient specific one model and the bone model through a virtual range of motion using the computer running the implant design software;
 h. comparing the virtual range of motion to desired kinematic data; and
 i. making adjustments to the design of the orthopedic implant using the computer running the implant design software in view of the desired kinematic data.

10. A method of designing an orthopedic implant, comprising the steps of:
 a. creating a 3D patient specific bone model using a computer running bone model software;
 b. registering an actual patient bone with the bone model using a computer running registration software;
 c. providing a database of orthopedic implant designs;
 d. selecting an orthopedic implant from a database of implant designs;
 e. providing a database of joint kinematics;
 f. applying the selected implant to the patient specific bone model;
 g. taking the orthopedic implant applied to the patient specific bone model and the bone model through a virtual range of motion using a computer running implant design software;
 h. comparing the virtual range of motion to desired kinematic data;
 i. making adjustments to the design of the orthopedic implant using the computer running implant design software in view of the desired kinematic data; and
 j. repeating steps a through h until achieving a desired result.

11. A method of selecting the optimal orthopedic implant for a specific patient, comprising the steps of:
 a. creating a 3D patient specific boric model using a computer running bone model software;
 b. registering an actual patient bone with the bone model using a computer running registration software;
 c. tracking the motion of the patient's actual bone through a range of motion;
 d. providing a database of orthopedic implant designs;
 e. selecting an orthopedic implant from a database of implant designs;
 f. providing a database of joint kinematics;
 g. applying the selected implant to the patient specific bone model;
 h. taking the orthopedic implant applied to the patient specific bone model through a virtual range of motion using a computer running implant design software;
 i. comparing the virtual range of motion to desired kinematic data;
 j. repeating, steps (a) through (i) a desired number of times; and
 k. choosing the implant that provides the best kinematic result.

12. A method of designing an orthopedic implant, comprising the steps of:
 a. creating a generic bone model;
 b. registering an actual patient bone with the one model;
 c. providing an orthopedic implant;
 d. implanting the orthopedic implant onto the patient's bone;
 e. providing a database of joint kinematics;
 f. taking the orthopedic implant and the bone model through a range of motion;
 g. tracking the motion of the implant and bone combination;
 h. comparing the actual motion of the implant and bone in combination to the kinematic database; and
 i. making adjustments to the design of the orthopedic implant in view of the desired kinematic data.

13. A method of selecting an orthopedic implant, comprising the steps of:
 a. creating a 3D patient specific bone model;
 b. registering an actual patient bone with the one model;
 c. providing an orthopedic implant;

d. implanting the orthopedic implant onto the patient's bone;
e. providing, a database of joint kinematics;
f. taking the orthopedic implant and the patient's bone model through a range of motion;
g. tracking the motion of the implant and bone combination;
h. comparing the actual motion of the implant and bone in combination to the kinematic database; and
i. making patient specific adjustments to the orthopedic implant in view of the desired kinematic data.

* * * * *